United States Patent
Wu et al.

(10) Patent No.: US 12,295,767 B2
(45) Date of Patent: May 13, 2025

(54) DETECTION APPARATUS AND IMAGING APPARATUS

(71) Applicant: SHANGHAI UNITED IMAGING HEALTHCARE CO., LTD., Shanghai (CN)

(72) Inventors: Yajun Wu, Shanghai (CN); Junjie Miao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 245 days.

(21) Appl. No.: 17/819,301

(22) Filed: Aug. 11, 2022

(65) Prior Publication Data
US 2023/0045875 A1    Feb. 16, 2023

(30) Foreign Application Priority Data

Aug. 11, 2021   (CN) .......................... 202121875410.2
Dec. 16, 2021   (CN) .......................... 202111547958.9

(51) Int. Cl.
*A61B 6/00*        (2024.01)

(52) U.S. Cl.
CPC .......... *A61B 6/4488* (2013.01); *A61B 6/4435* (2013.01)

(58) Field of Classification Search
None
See application file for complete search history.

(56) References Cited

U.S. PATENT DOCUMENTS

| | | | |
|---|---|---|---|
| 7,065,173 B2 | 6/2006 | Lacey et al. | |
| 7,102,308 B2 | 9/2006 | Lacey et al. | |
| 8,532,250 B2 | 9/2013 | Hashimoto et al. | |
| 8,987,673 B2 | 3/2015 | Hner et al. | |
| 9,086,360 B2 | 7/2015 | Joshi et al. | |
| 9,125,613 B2 | 9/2015 | Gregerson et al. | |
| 10,054,698 B2 | 8/2018 | Hefetz et al. | |
| 10,531,848 B2 | 1/2020 | Ikhlef | |
| 11,998,377 B2* | 6/2024 | Keller | A61B 6/037 |
| 2005/0117698 A1* | 6/2005 | Lacey | A61B 6/035 |
| | | | 378/19 |
| 2007/0053500 A1* | 3/2007 | Distler | A61B 6/035 |
| | | | 378/4 |
| 2009/0232281 A1* | 9/2009 | Jimbo | A61B 6/4488 |
| | | | 378/199 |
| 2011/0228910 A1* | 9/2011 | Gregerson | A61B 6/035 |
| | | | 324/309 |
| 2014/0153689 A1* | 6/2014 | Anno | A61B 6/4488 |
| | | | 29/401.1 |
| 2018/0275293 A1 | 9/2018 | Hefetz et al. | |
| 2019/0297717 A1* | 9/2019 | Kondo | H05G 1/025 |

(Continued)

FOREIGN PATENT DOCUMENTS

CN    108392218 A    8/2018
CN    211826539 U    10/2020

*Primary Examiner* — Marcus H Taningco
(74) *Attorney, Agent, or Firm* — METIS IP LLC

(57) ABSTRACT

The present disclosure provides a detection apparatus and an imaging apparatus. The detection apparatus may include an installation chamber, one or more detection units and a cooling assembly. The one or more detection units may be arranged in the installation chamber, and the installation chamber may include an air inlet and an air outlet. The cooling assembly may be configured to cool the one or more detection units.

19 Claims, 15 Drawing Sheets

(56) References Cited

U.S. PATENT DOCUMENTS

2020/0289074 A1 9/2020 Zilberstien et al.
2020/0315057 A1* 10/2020 Kuehn ................... A61B 6/035
2022/0229195 A1* 7/2022 Marsden .............. A61B 6/4233

* cited by examiner

DETECTION APPARATUS AND IMAGING APPARATUS

CROSS-REFERENCE TO RELATED APPLICATIONS

This application claims priority to Chinese Patent Application No. 202111547958.9, filed on Dec. 16, 2021, and Chinese Patent Application No. 202121875410.2, filed on Aug. 11, 2021, the contents of each of which are incorporated herein by reference in their entirety.

TECHNICAL FIELD

The present disclosure relates to the field of a medical imaging apparatus, in particular, to a detection apparatus and an imaging apparatus.

BACKGROUND

In a current cooling system of a detection apparatus of an imaging apparatus, a water cooling structure or an air cooling structure is usually used. The cooling effect of water cooling is good. However, the water cooling structure is complex, and the cost for the manufacturing and maintenance are high. The air cooling structure is simple, and the maintenance is convenient. However, the current air cooling structure cannot achieve a required cooling effect. Therefore, it is necessary to provide a cooling device with a good cooling effect and a simple structure for a detection apparatus.

SUMMARY

One aspect of the present disclosure may provide a detection apparatus. The detection apparatus may include an installation chamber including an air inlet and an air outlet; one or more detection units arranged in the installation chamber; and a cooling assembly configured to cool the one or more detection units.

In some embodiments, the installation chamber may be divided by one or more diaphragms into at least two sections.

In some embodiments, the installation chamber may be divided by the one or more diaphragms which are arranged along the direction of the one or more detection units.

In some embodiments, the installation chamber may be divided into three sections, and the three sections include a middle section, and two side sections located on both sides of the middle section.

In some embodiments, the cooling performance parameters of the cooling assembly acting on the middle section may be greater than the cooling performance parameters of the cooling assembly acting on the two side sections.

In some embodiments, the installation chamber may be divided by the one or more diaphragms into the at least two sections along the height direction of the one or more detection units.

In some embodiments, the detection apparatus may further include: a first diaphragm configured to divide the installation chamber into a first heat dissipation section and a second heat dissipation section; a first air assembly configured to dissipate heat from the first heat dissipation section; and a second air assembly configured to dissipate heat of the second heat dissipation section. At least a portion of the one or more detection units may be contained and fixed in the first heat dissipation section. The at least a portion of the one or more detection units may include a detection assembly. The rest portions of the one or more detection units may be contained and fixed in the second heat dissipation section.

In some embodiments, the installation chamber may be divided by a baffle assembly into an inlet section and an outlet section. The inlet section and outlet section may be respectively connected to opposing sides of the first heat dissipation section. The first air assembly may include at least one of an inlet air device arranged at the inlet section or an outlet air device arranged at the outlet section.

In some embodiments, the rest portions of the one or more detection units may include at least a portion of a heat dissipation assembly. The heat dissipation assembly may be in thermal contact with the detection assembly. The at least a portion of the heat dissipation assembly may extend to the second heat dissipation section; or an extension direction of the first heat dissipation section may be perpendicular to an extension direction of the second heat dissipation section.

In some embodiments, the heat dissipation assembly may include a support and a heat dissipation structure arranged on the support. The support may be in thermal contact with the detection assembly. Air flow generated by the second air assembly may flow in a direction parallel to a main heat dissipation plane of the support.

In some embodiments, the at least a portion of the one or more detection units may include a first circuit board module. The first circuit board module may be electrically connected and in thermal contact with the detection assembly. The rest portions of the one or more detection units may include a second circuit board module. The second circuit board module may be electrically connected with the first circuit board module and in thermal contacted with the support.

In some embodiments, the cooling assembly may include an air guiding assembly. The air guiding assembly may include one or more air ducts. At least one outlet end of the one or more air ducts may be connected with the air inlet of the installation chamber.

In some embodiments, the air guiding assembly may include a third air device, and air flow generated by the third air device may enter the installation chamber via the one or more air ducts.

In some embodiments, the air guiding assembly may include a shunt cover arranged between the third air device and the one or more air ducts. The shunt cover may be provided with one or more air outlet holes. At least one inlet end of the one or more air ducts may be connected with at least one of the one or more air outlet holes.

In some embodiments, a count of the air inlet may be one or more, which may be arranged on at least one of a side wall or a top wall of the installation chamber. The one or more air inlets may be arranged corresponding to a gap between two adjacent detection units of the one or more detection units.

In some embodiments, a first air duct may be formed between at least one of the one or more detection units and the top wall of the installation chamber. A second air duct and a third air duct through the at least one of the one or more detection units may be arranged on one side of the at least one of the one or more detection units. The first air duct and the second air duct may be both connected with the air inlet. The third air duct may be connected with the first air duct. The second air duct and the third air duct may be both connected with the air outlet.

In some embodiments, the cooling assembly may include an air guiding assembly. The air guiding assembly may include a plurality of air ducts. The installation chamber may be provided with one or more diaphragms configured to divide the installation chamber into at least two sections. There may be a plurality of air inlets. At least one of the at least two sections may be connected with a portion of the plurality of air ducts through a corresponding air inlet on the installation chamber.

In some embodiments, when the at least two sections are arranged along the direction of the one or more detection units. The cooling performance parameters of the cooling assembly acting on the middle section may be greater than the cooling performance parameters of the cooling assembly acting on at least one of the two side sections. When the at least two sections are arranged along a height direction of the one or more detection units, the cooling performance parameters of the cooling assembly acting on a section at an upper position may be greater than the cooling performance parameters of the cooling assembly acting on a section at a lower position. The cooling performance parameters of the cooling assembly may include at least one of a count of the air ducts, a count of air devices, and a speed of air devices corresponding to a section.

In some embodiments, the installation chamber may be divided by one or more diaphragms into at least two sections. The detection apparatus may further include temperature sensors arranged in different sections configured to detect temperatures of different sections. The cooling performance parameters of the cooling assembly acting on each section may be adjusted based on a temperature of a corresponding section.

Another aspect of the present disclosure may provide an imaging apparatus. The imaging apparatus may include: a rotating gantry and a detection apparatus. The detection apparatus may be arranged on the rotating gantry. The detection apparatus may include: an installation chamber including an air inlet and an air outlet; one or more detection units arranged in the installation chamber; and a cooling assembly configured to cool the one or more detection units.

BRIEF DESCRIPTION OF THE DRAWINGS

The present disclosure is further illustrated in terms of exemplary embodiments, and these exemplary embodiments are described in detail with reference to the drawings. These embodiments are not limited. In these embodiments, the same numeral indicates the same structure, wherein.

Figure 1:
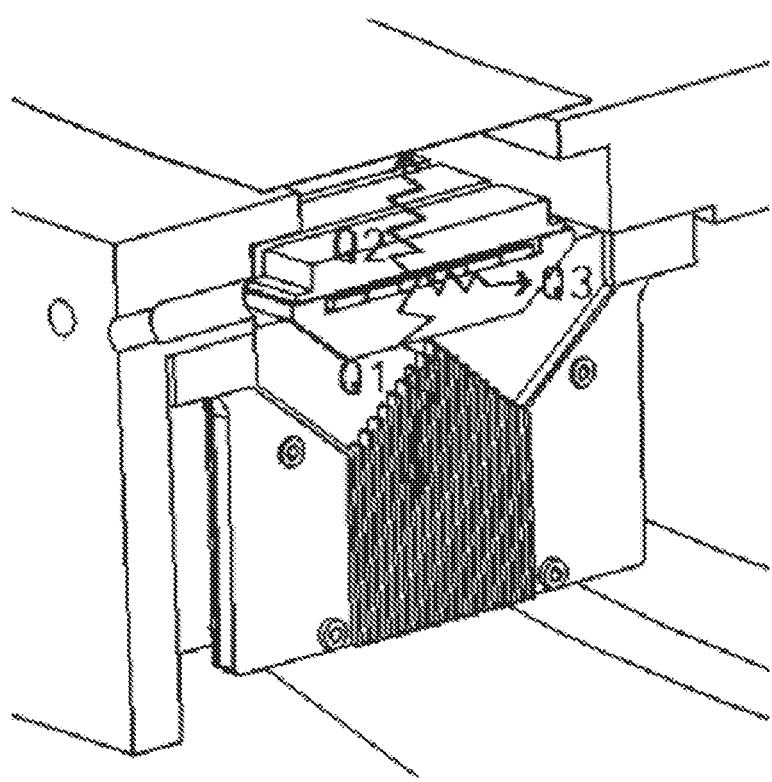
FIG. 1 is a schematic diagram illustrating heat dissipation of one or more detection units according to some embodiments of the present disclosure.

Numerals in drawings may refer to the following structures: 1000—imaging apparatus; 100—detection apparatus; 200—rotating gantry; 10—housing assembly; 11—first housing; 12—second housing; 13—first plane; 14—side plane; 15—second plane; 16—side plane; 17—end plane; 18—end plane; 20—installation chamber; 21—first heat dissipation section; 22—second heat dissipation section; 23—inlet section; 24—outlet section; 25, 25a, 25b—air inlet; 26, 26a, 26b—air outlet; 30—detection unit; 31—detection assembly; 311—detection module; 312—anti-scatter grid; 32—heat dissipation assembly; 321—support; 3211—diaphragm part; 3212—heat dissipation diaphragm; 322—heat dissipation fin; 33—circuit board assembly; 331—first circuit board module; 332—second circuit board module; 34—windshield; 40—cooling assembly; 41—first air assembly; 411—inlet air device; 412—outlet air device; 42—second air assembly; 421—second air device; 43—air guiding assembly; 431—air duct; 432—third air device; 433—shunt cover; 434—air outlet hole; 51—first air duct; 52—second air duct; 53—third air duct; 54—fourth air duct; 55—fifth air duct; 60—diaphragm; 61—first diaphragm; 70—baffle assembly; 71—first baffle plate; 72—second baffle plate; 73—third baffle plate; 81—inlet flow channel; 82—outlet flow channel.

DETAILED DESCRIPTION

In order to illustrate the technical solutions related to the embodiments of the present disclosure, brief introduction of the drawings referred to in the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

It will be understood that the terms "system," "device," "unit," and/or "module" used herein are one method to distinguish different components, elements, parts, sections, or assemblies of different levels in ascending order. However, the terms may be displaced by other expressions if they may achieve the same purpose.

As shown in the present disclosure and claims, unless the context clearly indicates exceptions, the words "a," "an," "one," and/or "the" do not specifically refer to the singular, but may also include the plural. The terms "including" and "comprising" only suggest that the steps and elements that have been clearly identified are included, and these steps and elements do not constitute an exclusive list, and the method or device may also include other steps or elements.

An imaging apparatus may be applied in various fields, such as healthcare industry (e.g., medical application), security application, industrial application, etc. For example, the imaging apparatus may be used for internal inspection of a component, such as defect detection, safety scanning, fault analysis, metrology, assembly analysis, void analysis, wall thickness analysis, or the like, or any combination thereof. The imaging apparatus may include a computer tomography (CT) apparatus, a digital radiography (DR) apparatus, a computer radiography (CR) apparatus, a multimodal apparatus, or the like, or any combination thereof.

An imaging apparatus may include a detection apparatus. The detection apparatus may include one or more detection units. The imaging apparatus may generate a signal by scanning an object with a ray beam. The one or more detection units in the imaging apparatus may generate a signal by detecting the ray beam passing through the object. Since the intensity of power (total power/area of the imaging apparatus) is high and the thermal conductivity of a material of the imaging apparatus is low, heat may be accumulated during the operation of the one or more detection units, affecting the image quality. In addition, due to large sizes in a length direction (corresponding to a direction Y of the one or more detection units) and a width direction (corresponding to a width direction X of the one or more detection units) of a detection module composed of the one or more detection units, a problem of temperature gradient may occur between different portions of the detection module. The temperature gradient of the detection apparatus may cause inconsistent responses of different detection units, resulting in an abnormality of the detection apparatus and affecting the image quality.

FIG. 1 is a schematic diagram illustrating heat dissipation of one or more detection units according to some embodiments of the present disclosure. In some embodiments, a detection assembly of one or more detection units may produce a lot of heat during operation, and the heat may be transferred outward through three ways: conduction, convection, and radiation, and heat corresponding to the three ways may be represented as: Q1, Q2 and Q3, respectively. As shown in FIG. 1, a portion of heat Q1 may be transferred to a support with solid heat conduction, and a portion of heat Q2 may be transferred to air in an installation chamber by convection with the air. The heat Q2 may change with a change of a thermal power of the detection assembly, and different work states may lead to different thermal powers of the detection assembly. The accumulation of the heat Q2 may cause the temperature of the detection assembly to rise, thus the image quality may be affected. The change of the heat Q2 may also cause the detection assembly to work in an alternating ambient temperature, affecting the long-term reliability of the detection assembly.

A detection apparatus provided in some embodiments of the present disclosure may include an installation chamber and a cooling assembly. The cooling assembly may be configured to cool one or more detection units arranged in the installation chamber, improving the effect of cooling and heat dissipation without affecting the lightproof requirement. Further, the installation chamber may be divided into a plurality of sections by diaphragms. The plurality of sections may be used to dissipate heat independently, improving the temperature control accuracy and heat dissipation efficiency. Additionally or alternatively, air flow may be directly supplied to a region in the installation chamber where air generated by an air device is difficult to reach directly by setting an air guiding assembly, thus the heat dissipation efficiency may be improved. The detection apparatus provided in some embodiments of the present disclosure may bring heat Q1 transmitted by the detection unit(s) with heat conduction and heat Q2 accumulated in the installation chamber out of the detection apparatus in time, thus a problem of heat dissipation of the detection apparatus of high power intensity may be solved, and the stability of a working environment temperature of the detection apparatus may be maintained.

Figure 2:
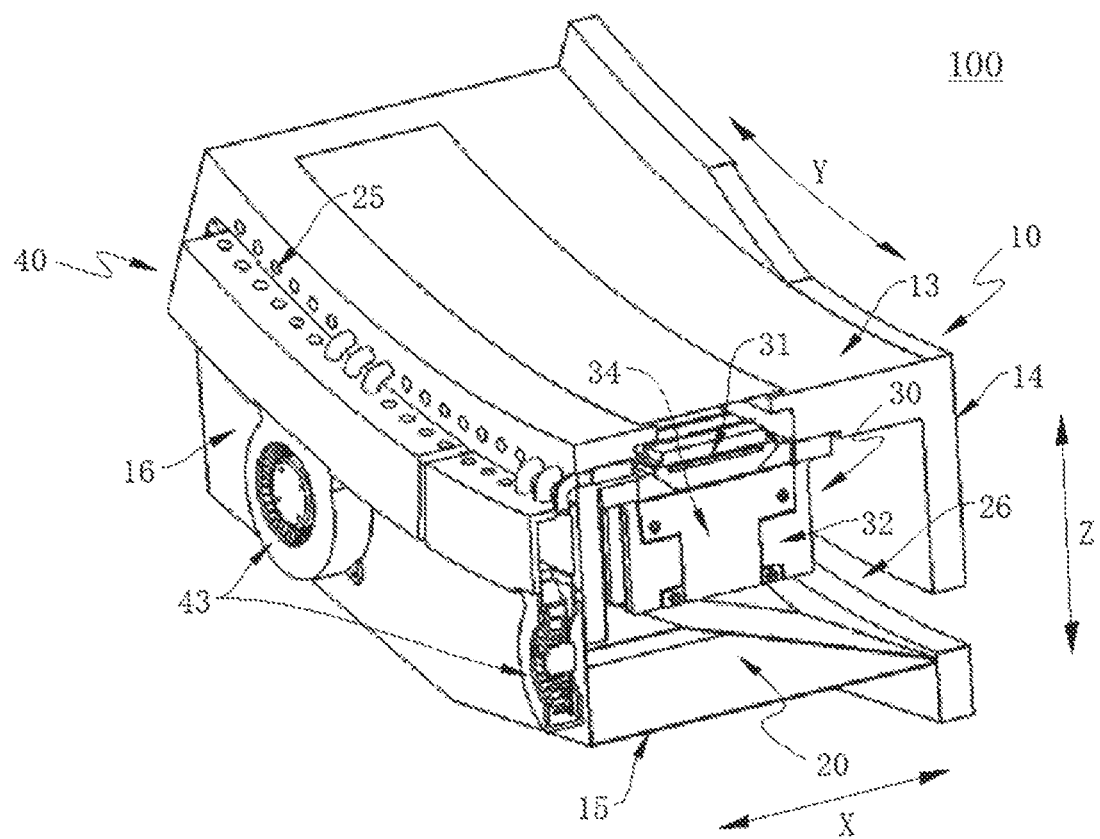
FIG. 2 is a schematic diagram illustrating a structure of a detection apparatus according to some embodiments of the present disclosure.

FIG. 2 is a schematic diagram illustrating a structure of a detection apparatus 100 according to some embodiments of the present disclosure. The detection apparatus 100 provided in some embodiments of the present disclosure may be described in detail below. It should be noted that the following embodiments are merely used to illustrate the present disclosure, and may not limit the scope of the present disclosure.

As shown in FIG. 2, the detection apparatus 100 may include an installation chamber 20 and one or more detection units 30. The installation chamber 20 may be provided with an air inlet 25 and an air outlet 26. The one or more detection units 30 may be arranged in the installation chamber 20. The detection apparatus 100 may also include a cooling assembly 40 configured to cool the one or more detection units 30.

Figure 3:
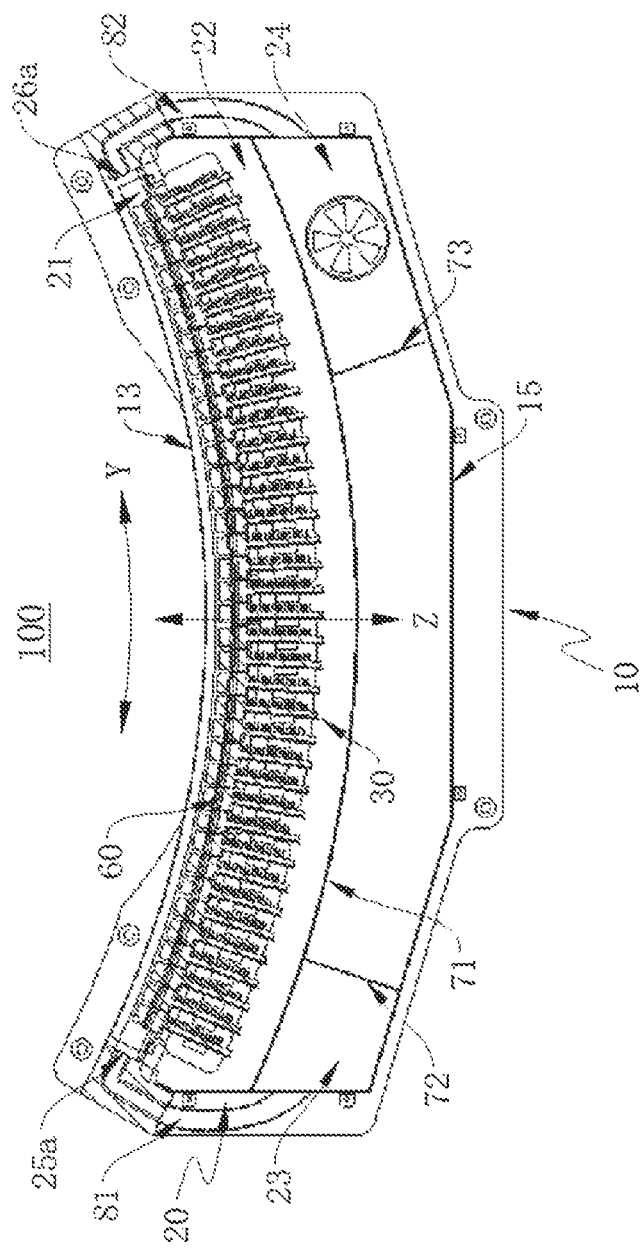
FIG. 3 is a sectional view illustrating a detection apparatus according to some embodiments of the present disclosure.

FIG. 3 is a sectional view illustrating the detection apparatus 100 according to some embodiments of the present disclosure.

The one or more detection units 30 may be configured to detect a detection signal of a ray beam passing through an object, and process the detection signal. In some embodiments, the one or more detection units 30 may include a detection assembly 31. The detection assembly 31 may be configured to receive the detection signal. The detection signal may be an X-ray signal or other types of signals. In some embodiments, the one or more detection unit 30 may also include a circuit board assembly 33. The circuit board assembly 33 may implement functions relating to detection signal processing. For example, the circuit board assembly 33 may convert an electrical signal into a digital signal for further processing. In some embodiments, the circuit board assembly 33 may be electrically connected to a detection module 311. In some embodiments, the one or more detection units 30 may also include a heat dissipation assembly 32. The heat dissipation assembly 32 may be configured to dissipate heat generated on the detection assembly 31 and/or the circuit board assembly 32, and support the one or more detection units 30. The heat dissipation assembly 32 may be in thermal contact with the detection assembly 31 and/or the circuit board assembly 33. It should be noted that the thermal contact may refer to a relatively good heat transfer between two interconnected assemblies. For example, a sufficient heat transfer may be implemented between two assemblies with direct contact, or the sufficient heat transfer may be implemented between the two assemblies with indirect contact through a thermal medium (e.g., a metal thermal pad, a thermal silicone grease, etc.).

A count and arrangement of the one or more detection units 30 may be determined based on a detection range, a signal quality, or other factors required by the detection apparatus 100. In some embodiments, the detection apparatus 100 may include a plurality of detection units 30. As shown in FIG. 3, the plurality of detection units 30 may be spaced side by side along an arc, such that the plurality of detection units 30 may be arranged in an arc shape. The detection range of the detection apparatus 100 may be located at a side where the plurality of detection units 100 are towards a center of the arc. In some other embodiments, the detection apparatus 100 may include one detection unit 30. The detection unit 30 may include a plurality of detection assemblies 31 spaced side by side along an arc, such that the detection unit 30 may be arranged in an arc shape. The detection range of the detection apparatus 100 may be located at a side where the detection unit 30 is towards a center of the arc. It should be understood that in some other embodiments, the one or more detection units 30 may be arranged in other ways, such as in a straight line, as long as the detection range and the signal quality of the detection apparatus 100 may meet a predetermined requirement. More descriptions of the detection unit(s) 30 may be found elsewhere in the present disclosure, for example FIGS. 9-14 and/or the descriptions thereof.

The installation chamber 20 may be a chamber configured to hold components such as the one or more detection units 30. The installation chamber 20 may be a lightproof closed or semi-closed space. In some embodiments, the installation chamber 20 may be formed in a housing assembly 10. The housing assembly 10 may be configured to install various components of the detection apparatus 100 and connect the detection apparatus 100 as a whole to other components of the imaging apparatus.

Figure 4:
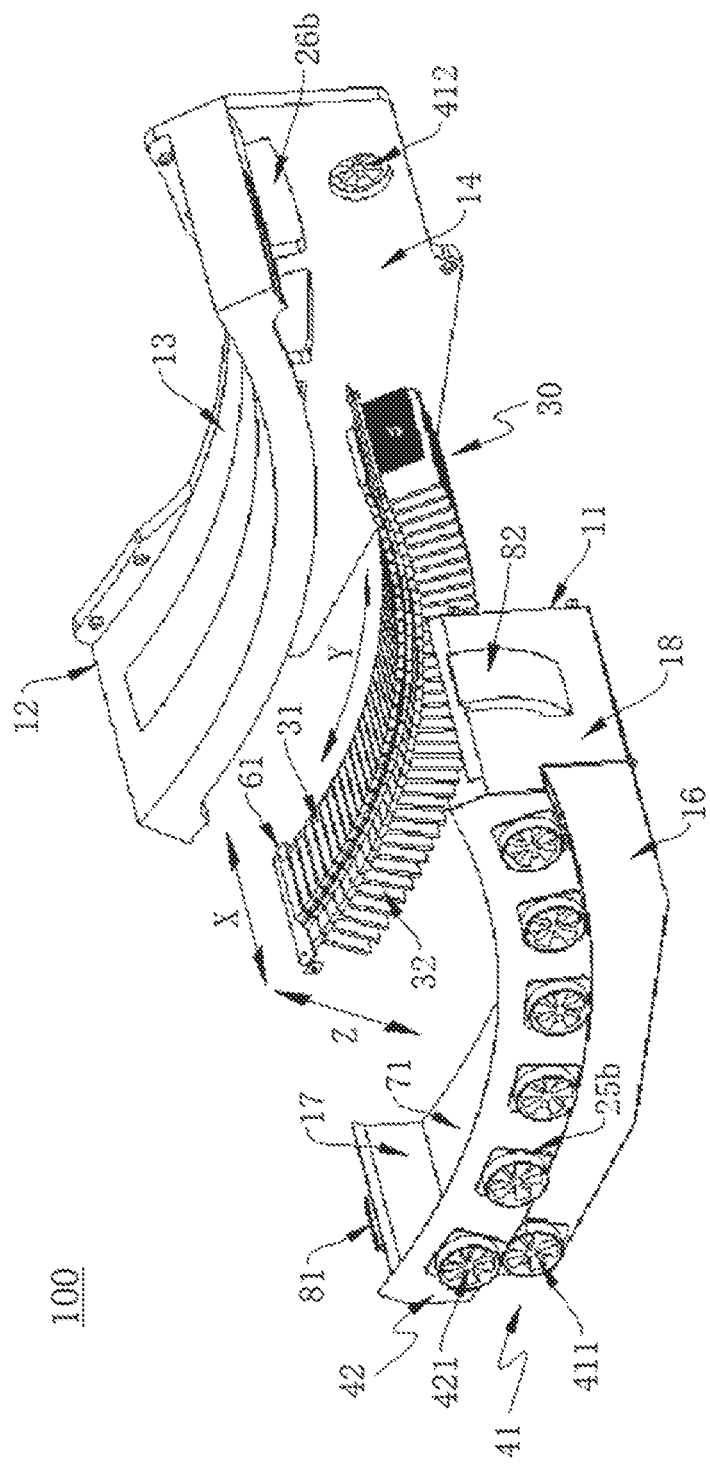
FIG. 4 is a schematic diagram illustrating an installation and an uninstallation of a detection apparatus according to some embodiments of the present disclosure.
Figure 5:
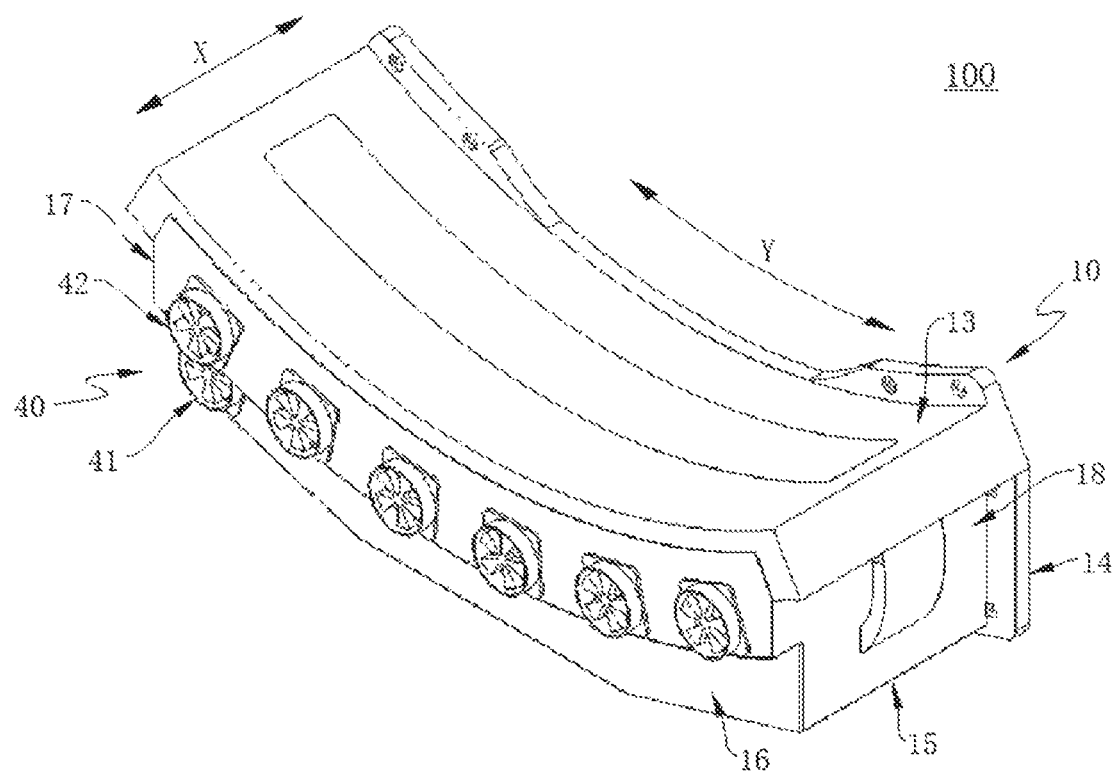
FIG. 5 is a schematic diagram illustrating a structure of a detection apparatus according to some embodiments of the present disclosure.

FIG. 4 is a schematic diagram illustrating an installation and an uninstallation of a detection apparatus according to some embodiments of the present disclosure. FIG. 5 is a schematic diagram illustrating a structure of a detection apparatus according to some embodiments of the present disclosure.

A shape of the installation chamber 20 and/or a shape of the housing assembly 10 may be determined based on an arrangement of components such as the one or more detection units 30, or a space requirement and a shape requirement for installation. In some embodiments, the shape of the housing assembly 10 may be a portion of an annulus (also referred to as an annular sector). For example, as shown in FIG. 3, a sectional view of the housing assembly 10 and a sectional view of the installation chamber 20 are roughly annular sectors, respectively. In some embodiments, as show in the sectional view in FIG. 3, a periphery of the housing assembly 10 may form a detection space of an annular sector shape. In the same plane, a plurality of housing assemblies 10 may be connected in sequence and form a detection space of a shape of annulus. As shown in FIG. 3, the housing assembly 10 may include a first plane 13 facing the detection space and a second plane 15 opposing the detection space. Both the first plane 13 and the second plane 15 may be curved surfaces of arc-shapes. The first plane 13 and the second plane 15 may be roughly parallel to each other. As shown in FIG. 4, the housing assembly 10 may also include side planes 14 and 16 arranged along an axial direction of the detection space and end planes 17 and 18 arranged along a circumferential direction of the detection space.

It should be understood that in some other embodiments, the installation chamber 20 and/or the housing assembly 10 may be designed as other shapes, such as a cuboid shape, a cylindrical shape, etc., based on the arrangement of components such as the one or more detection units 30, or the space requirement and the shape requirement for installation.

The forming manner of the housing assembly 10 may be determined based on the installation and maintenance requirement of components such as the one or more detection units 30. In some embodiments, the housing assembly 10 may be formed by connecting a plurality of plates. For example, as shown in FIG. 4 and FIG. 5, the housing assembly 10 may include a first housing 11 and a second housing 12 connected to each other. The first housing 11 may roughly correspond to the second plane 15 of the housing assembly 10, the side plane 16, and the end planes 17 and 18 that are arranged along the circumference of the detection space. The second housing 12 may roughly correspond to the first plane 13 and the side plane 14 of the housing assembly 10. The second housing 12 and the first housing 11 may be fixed to each other to form the installation chamber 20, and roughly form a hexahedral hollow structure.

It should be understood that in some other embodiments, the housing assembly 10 may be formed with other forming manners based on the installation and maintenance requirement of components such as the one or more detection units 30, such as an integrated forming manner.

In some embodiments, the installation chamber 20 may be provided with one or more diaphragms 60 configured to divide the installation chamber 20 into at least two sections. In some embodiments, gas may be supplied into each section from the outside. For example, each section may be connected with other air flow generators of the imaging apparatus. In some other embodiments, the cooling assembly 40 may be provided with the same device or different devices configured to generate air flow, such as air devices or air devices with a refrigeration function, to supply air and dissipate heat, thus the heat dissipation effect and efficiency may be improved. It should be noted that the air devices (e.g., an inlet air device 411, an outlet air device 412, a second air device 421, a third air device 432, etc.) are devices that rely on input mechanical energy to increase gas pressure and discharge gas. The air devices may include an axial flow air device, a blower, a centrifugal air device, etc. In some embodiments, an air device of the cooling assembly 40 may compress air and supply the compressed air into the installation chamber 20 or the sections divided from the installation chamber 20. More descriptions of the air devices and sections of the installation chamber 20 may be found below, which are not repeated herein.

The manner for dividing the sections may be determined based on an actual requirement. In some embodiments, the manner for dividing the installation chamber may be determined based on lightproof requirements, heat dissipation requirements, etc., of different components of the one or more detection units 30. For different components of each detection unit 30, such as the detection assembly 31 and the heat dissipation assembly 32, the detection assembly 31 may receive the detection signal, and compared to the heat dissipation assembly 32, the detection assembly 31 may have high lightproof requirements and be sensitive to temperature (a large temperature fluctuation of the detection assembly 31 may lead to an abnormal response of the detection assembly 31). Different components of the detection unit 30 may be arranged in different sections for refined cooling and heat dissipation, thus the temperature control accuracy and heat dissipation efficiency may be improved, the temperature gradient of the detection unit 30 may be reduced, and the working stability and the detection accuracy of the detection apparatus 100 may be ensured.

In some embodiments, the one or more diaphragms 60 may divide the installation chamber 20 along the height direction Z of the one or more detection units 30. In some embodiments, a count of the diaphragm(s) 60 may be one and a count of the sections may be two. The installation chamber 20 may be provided with a single diaphragm 60 (e.g., the first diaphragm 61). Along the height direction Z of the one or more detection units 30, the diaphragm 60 may divide the installation chamber 20 into a first heat dissipation section 21 and a second heat dissipation section 22. For example, as shown in FIG. 3, the first diaphragm 61 may be roughly a plate-shaped structure. The first diaphragm 61 may extend along the direction Y of the one or more detection units 30, and cooperate with the heat dissipation assembly 32 to roughly divide the installation chamber 20 into the first heat dissipation section 21 and the second heat dissipation section 22 that are arranged parallel in the height direction. In some embodiments, for each detection unit 30, at least a portion of the detection unit 30 (e.g., the detection assembly 31) may be contained and fixed in the first heat dissipation section 21, and the rest portions of the detection unit 30 (e.g., the heat dissipation assembly 32 and/or the circuit board assembly 33) may be contained and fixed in the second heat dissipation section 22.

It should be understood that in some other embodiments, the count of the diaphragm(s) 60 may be two or more. Along the height direction Z of the one or more detection units 30, the count of the sections divided from the installation chamber 20 may be three or more. The count of the diaphragm(s) 60 and the count of the sections may be determined based on an actual requirement.

In some other embodiments, the manner for dividing the installation chamber 20 may be determined based on the density and/or heat dissipation of the components in the installation chamber 20. For the one or more detection units 30, detection unit(s) 30 in different regions may be arranged in different sections for refined cooling and heat dissipation. For the detection unit(s) 30 spaced in the installation chamber 20, detection unit(s) 30 in a middle region in a distribution route of the arrangement of the one or more detection units 30 may be spaced by equal intervals in sequence. A space between detection unit(s) 30 in side regions on both sides of the distribution route and a wall of the installation chamber 20 may be greater than a space between two adjacent detection units 30. On the distribution route of the detection unit(s) 30, the density of the detection unit(s) 30 in the middle region may be greater than the density of the detection unit(s) 30 in the side regions, so that the heat accumulation rate and the difficulty of heat dissipation through thermal convection in the middle region may be higher than the heat accumulation rate and the difficulty of heat dissipation through thermal convection in the side regions. By arranging the detection unit(s) 30 in the middle region and the detection unit(s) 30 in the side regions in different sections, the heat dissipation efficiency may be improved, the temperature gradient between different detection units 30 may be reduced, and the stability and detection accuracy of the detection apparatus 100 may be improved.

In some embodiments, the one or more diaphragms 60 may divide the installation chamber 20 along the direction Y of the one or more detection units 30. In some embodiments, the count of diaphragm(s) 60 may be one and the count of the sections may be two. In some other embodiments, the count of diaphragm(s) 60 may be two and the count of the sections may be three. Further, two diaphragms 60 (e.g., the second diaphragm and the third diaphragm) may be arranged in the installation chamber 20. Along the direction Y of the one or more detection units 30, the two diaphragms 60 may divide the installation chamber 20 into a middle section and two side sections, and the two side sections may located on both sides of the middle section. It should be noted that the middle section may refer to a section formed by the two diaphragms 60 and the housing assembly 10, and a side section may refer to a section formed by one diaphragm 60 and the housing assembly 10. A density of components contained in the middle section may be greater than a density of components contained in at least one of the two side sections. For example, on the distribution route of the one or more detection units 30, the detection unit(s) 30 in the middle region may be contained in the middle section, and the detection unit(s) 30 in the side regions may be contained in the two side sections, respectively.

In some embodiments, when the one or more detection units 30 are arranged along a curve, a direction of the diaphragm 60 may be perpendicular to a tangent of an intersection of the curve and the diaphragm 60. When the one or more detection units 30 are arranged along a straight line, the direction of the diaphragm 60 may be perpendicular to the straight line. In some other embodiments, the direction of the diaphragm 60 may be determined based on an actual requirement as long as the installation chamber 20 may be divided along the arrangement direction Y of the one or more detection units 30. For example, the direction of the diaphragm 60 may be perpendicular to the horizontal plane.

It should be understood that in some other embodiments, the installation chamber 20 may be divided in other manners based on the actual requirement. For example, a plurality of diaphragms 60 may divide the installation chamber 20 along the direction Y and the height direction Z of the one or more detection units 30 simultaneously, which may not be limited herein.

An air flow direction in the installation chamber 20 may affect the heat dissipation efficiency of the detection apparatus 100. In some embodiments, when the installation chamber 20 is divided into at least two sections, an extension direction of a section may affect the air flow direction, so that air flow directions in two adjacent sections may be different.

In some embodiments, the installation chamber 20 may be divided into the first heat dissipation section 21 and the second heat dissipation section 22. An extension direction of the first heat dissipation section 21 may be perpendicular to an extension direction of the second heat dissipation section 22. Thus, the extension direction of the section may affect the air flow direction. For example, the air may be guided to flow along the extension direction of the section. Since the extension directions of the two sections may be perpendicular to each other, the air flow direction in the first heat dissipation section 21 may be perpendicular to the air flow direction in the second heat dissipation section 22. The fluid flowing in the first heat dissipation section 21 may take away the heat of the detection assembly 31 and the circuit board assembly 33 in time. The fluid flowing in the second heat dissipation section 22 may take away the heat on the heat dissipation assembly 32 (the heat from the detection assembly 31 and the circuit board assembly 33) in time. In addition, the extension direction of the first heat dissipation section 21 and the extension direction of the second heat dissipation section 22 may be perpendicular to each other, facilitating mutual heat dissipation between the fluid in the two sections.

It should be understood that in some other embodiments, an included angle between air flow directions of two adjacent sections may be determined based on an actual requirement, such as 20°, 40°, 60° or 80°.

In some other embodiments, when the installation chamber 20 is divided into at least two sections, extension directions of the at least two sections may affect air flow directions, and air flow directions in two adjacent sections may be the same. In some embodiments, the installation chamber 20 may be divided into the first heat dissipation section 21 and the second heat dissipation section 22. The extension direction of the first heat dissipation section 21 may be parallel to the extension direction of the second heat dissipation section 22. Thus, the extension directions of the two sections may be the same, the air of the two sections may be guided to flow in the same direction. The air flow direction in the first heat dissipation section 21 may be parallel to the air flow direction in the second heat dissipation section 22.

In some embodiments, a baffle assembly 70 may be provided in the installation chamber 20 to divide the installation chamber 20 into an inlet section 23 and an outlet section 24. The inlet section 23 and the outlet section 24 may be respectively connected with both sides of a portion or all of the at least two sections. The cooling assembly 40 may be cooperated with the inlet section 23 and the outlet section 24, and air may enter into or out of the sections divided from the installation chamber 20 through the inlet section 23 and the outlet section 24. Thus, the structures of the sections may meet the lightproof requirement and the requirement of heat dissipation efficiency simultaneously.

In some embodiments, when the installation chamber 20 is divided into the first heat dissipation section 21 and the second heat dissipation section 22 along the height direction Z of the one or more detection units 30, as shown in FIG. 3, the inlet section 23 and the outlet section 24 are respectively connected with both sides (e.g., the end plane 17 and the end plane 18 of the housing assembly 10) of the first heat dissipation section 21. Thus, the first heat dissipation section 21, the inlet section 23, and the outlet section 24 may form an integrated and connected heat dissipation channel. On the one hand, by connecting the inlet section 23 and the outlet section 24, the first heat dissipation section 21 may be indirectly connected with the outside, facilitating the first heat dissipation section 21 to meet the lightproof requirement and the requirement of heat dissipation efficiency simultaneously, and ensuring the working stability of components (e.g., the detection assembly 31) of the one or more detection units 30 contained in the first heat dissipation section 21. On the other hand, various components of the cooling assembly 40 acting on the first heat dissipation section 21 (e.g., the first air assembly 41) may be arranged or directly act on the inlet section 23 and/or the outlet section 24 without compressing or adjusting the first heat dissipation section 21, thus the structure of the first heat dissipation section 21 may be optimized.

In some embodiments, the baffle assembly 70 may include a first baffle plate 71, a second baffle plate 72, and a third baffle plate 73. The first baffle plate 71 may be arranged between the first plane 13 and the second plane 15 of the housing assembly 10. The first baffle plate 71 may be located between the diaphragm 60 (e.g., the first diaphragm 61) and the second plane 15 of the housing assembly 10 to divide the installation chamber 20 into the third section. The first baffle plate 71 may be roughly parallel to the first plane 13. The second baffle plate 72 and the third baffle plate 73 may be arranged in a direction perpendicular to the first plane 13. The third section may be divided into the inlet section 23 and the outlet section 24. The space of the second heat dissipation section 22 may be relatively reduced, improving the convection and heat dissipation efficiency of the second heat dissipation section 22.

It should be understood that in some other embodiments, the count and position of the baffle assembly 70 may be determined based on an actual requirement. For example, the second baffle plate 72 and the third baffle plate 73 may be designed as a single baffle plate, as long as the installation chamber 20 is divided into the inlet section 23 and the outlet section 24.

As shown in FIG. 3, in some embodiments, along the height direction Z of the one or more detection units 30, the second heat dissipation section 22 may be located among the first heat dissipation section 21, the inlet section 23, and the outlet section 24. The second heat dissipation section 22 may separate the first heat dissipation section 21 from the inlet section 23 and the outlet section 24, so that various electrical components (e.g., the first air assembly 41) of the cooling assembly 40 may be relatively far away from the detection assembly 31. Thus, the impact of the various electrical components on the detection signal of the detection assembly 31 may be reduced. In some embodiments, the first heat dissipation section 21 and the second heat dissipation section 22 may be arranged along the direction Y of the one or more detection units 30 to control a total volume of the housing assembly 10.

In some embodiments, the inlet section 23 may be connected with one side of the first heat dissipation section 21 through an inlet flow channel 81. The outlet section 24 may be connected with another side of the first heat dissipation section 21 through an outlet flow channel 82. It should be understood that the inlet flow channel 81 and the outlet flow channel 82 may be flow channels opened in the housing assembly 10, or may be flow channels connected with the outside of the housing assembly 10. As shown in FIG. 4, in some embodiments, the inlet flow channel 81 and the outlet flow channel 82 may respectively have a shape of arc and be formed outside the first housing 11 solely. There may be a space between an outer wall of the inlet flow channel 81 and the first housing 11 and a space between the outlet flow channel 82 and the first housing 11, respectively. Thus, temperatures of the air in the inlet passage 25 and the outlet passage 26 may be not affected by the temperature of the air in the second heat dissipation section 22.

In some embodiments, the inlet flow channel 81 and the outlet flow channel 82 may be arranged on both sides of the first heat dissipation section 21 along the direction Y of the one or more detection units 30. It should be understood that in some other embodiments, the inlet flow channel 81 and the outlet flow channel 82 may be arranged at other positions based on positions of an air inlet 25a and an air outlet 26b of the first heat dissipation section 21. For example, the inlet flow channel 81 and the outlet flow channel 82 may be arranged on both sides of the first heat dissipation section 21 along the width direction X of the one or more detection units 30, as long as the air flow direction of the first heat dissipation section 21 meets an actual requirement. More descriptions of the positions of the air inlet 25 and air outlet 26 may be found below, which are not repeated herein.

In some embodiments, the cooling assembly 40 may include a first air assembly 41 configured to dissipate heat from the first heat dissipation section 21. In some embodiments, the first air assembly 41 may include an inlet air device 411 arranged in the inlet section 23 configured to pump external fluid into the first heat dissipation section 21.

The first air assembly 41 may include an outlet air device 412 arranged in the outlet section 24 for discharging the fluid in the first heat dissipation section 21.

As shown in FIG. 4, in some embodiments, the inlet air device 411 may be correspondingly arranged at an inlet of the inlet section 23, and the outlet air device 412 may be correspondingly arranged at an outlet of the outlet section 24, thereby improving the air supply efficiency. In some embodiments, a count of the inlet air device 411 and/or a count of the outlet air device 412 may be one or more. It should be understood that in some other embodiments, the inlet air device 411 and the outlet air device 412 may also be arranged at other positions, such as in the inlet section 23 and outlet section 24, or outside the inlet section 23 and outlet section 24 (e.g., in connection with other structures of the imaging apparatus). Additionally or alternatively, the inlet air device 411 and the outlet air device 412 may be directly arranged at the air inlet 25a of the first heat dissipation section 21 or at the periphery of the air inlet 25a. The outlet air device 412 may be directly arranged at the air outlet 26a of the first heat dissipation section 22 or at the periphery of the air outlet 26a. Accordingly, the inlet section 23, the outlet section 24, the inlet flow channel 81, and the outlet flow channel 82 may be be omitted, as long as the heat dissipation requirement of the first heat dissipation section 21 is met.

As shown in FIG. 3 and FIG. 4, in some embodiments, for the second heat dissipation section 21 divided from the installation chamber 20 along the height direction Z of the one or more detection units 30, the cooling assembly 40 may be provided with a second air assembly 42 configured to dissipate heat from the second heat dissipation section. The second air assembly 42 may include a second air device 421. It should be understood that in some embodiments, the second air device 421 may be arranged at an air inlet 25b and/or an air outlet 26b of the second heat dissipation section 22, arranged inside the second heat dissipation section 22, or arranged outside the second heat dissipation section 22 (e.g., in connection with other structures of the imaging apparatus). A count of the second air device 421 may be one or more, as long as the count of the second air device 421 meets the heat dissipation requirement of the second heat dissipation section 22.

The air inlet 25 may be a through hole on a wall of the installation chamber 20. The air inlet 25 may be configured to supply air flow from the outside of the installation chamber 20 to the inside of the installation chamber 20. In some embodiments, the air inlet 25 may be of any size and shape that meets an actual requirement. For example, the shape of the air inlet 25 may a circle, a triangle, a square, a polygon, or the like, or any combination thereof.

In some embodiments, the position of the air inlet 25 may correspond to a position of a component (e.g., the one or more detection units 30) in the installation chamber 20 that needs to be cooled, facilitating supplying air to the component. In some embodiments, the one or more detection units 30 may be arranged on a top wall (e.g., the first plane 13 of the housing assembly 10) of the installation chamber 20. The air inlet 25 may be arranged on the top wall of the installation chamber 20 and/or side wall(s) (e.g., the side plane 16 and/or the side plane 14 of the housing assembly 10) of the installation chamber 20 located on one or both sides of the detection unit 30, facilitating supplying air to the one or more detection units 30. In some other embodiments, the air inlet 25 may also be arranged on end wall(s) (such as the end plane 17 and/or the end plane 18 of the housing assembly 10) of the installation chamber 20 at one or both ends of the one or more detection units 30, as long as the air inlet 25 may supply air flow to the one or more detection units 30.

It should be understood that the detection apparatus 100 may allow the ray beam to penetrate at least a portion of a wall (e.g., the top wall) of the installation chamber 20. A component for detecting the ray beam in the one or more detection units 30 may be located close to the wall that allows the ray beam to penetrate, facilitating the reception of the detection signal. In some embodiments, the air inlet 25 may keep away from the wall that allows the ray beam to penetrate and be arranged on other walls of the installation chamber 20 to avoid affecting the imaging effect.

In some embodiments, the position of the air inlet 25 may be correspond to a gap between two adjacent detection units 30, so that the air inlet 25 may guide the air flow through the gap between the two adjacent detection units 30 without being blocked by the two detection units 30, thereby reducing the wind resistance and improving the heat dissipation efficiency.

Figure 6:
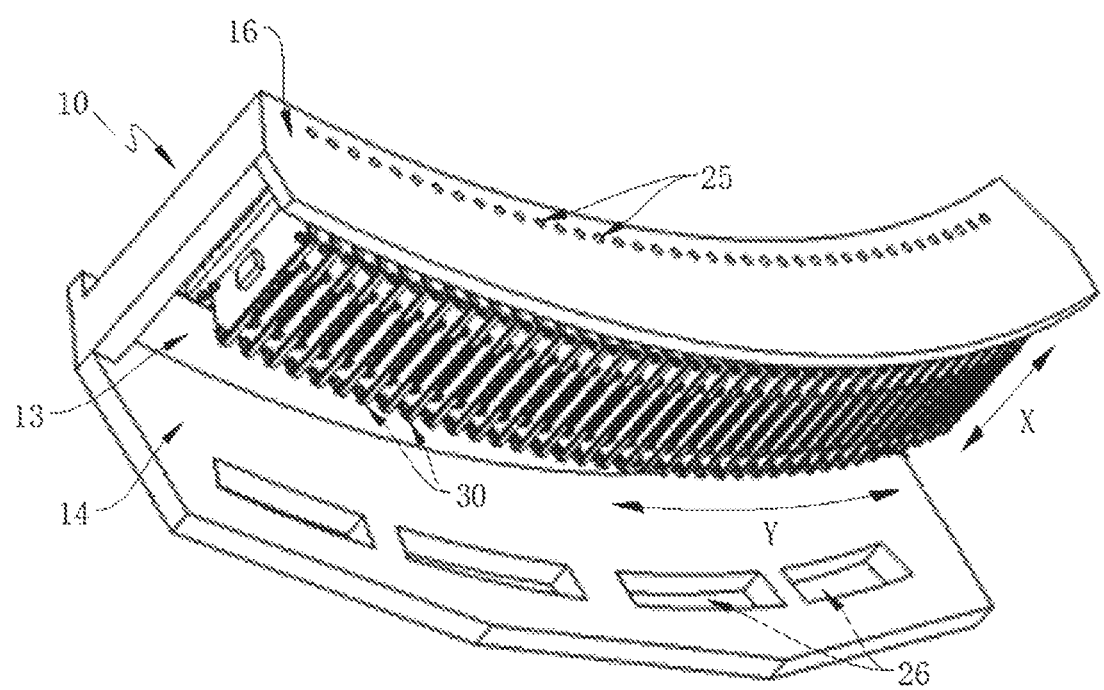
FIG. 6 is a schematic diagram illustrating an installation structure of a detection apparatus according to some embodiments of the present disclosure.

FIG. 6 is a schematic diagram illustrating an installation structure of a detection apparatus 100 according to some embodiments of the present disclosure. For example, as shown in FIG. 6, the air inlet 25 may be arranged on the side plane 16 of the housing assembly 10 and be aligned with the detection assembly 31 of the one or more detection units 30 to guide the air flow. As another example, as shown in FIG. 3 and FIG. 4, the installation chamber 20 may be divided into two sections along the height direction Z of the one or more detection units 30. The air inlet 25a of the first heat dissipation section 21 may be arranged on the end plane 17 of the housing assembly 10 and be aligned with the detection assembly 31 of the detection unit(s) 30 to guide the air flow. The air inlet 25b of the second heat dissipation section 22 may be arranged on the side plane 16 of the housing assembly 10 and be aligned with the gap between the two adjacent detection units to guide the air flow. As a further example, the installation chamber 20 may be divided into three sections along the direction Y of the one or more detection units 30. An air inlet 25 of each of the three sections may be arranged on the side plane 14 and side plane 16 of the housing assembly 10 and be aligned with a gap between two adjacent detection units to guide the air flow.

In some embodiments, a count of the air inlet 25 may be one or more. When the installation chamber 20 is divided into at least two sections, each of the at two sections may be provided with at least one air inlet 25. When there is multiple air inlets 25, the multiple air inlets 25 may be arranged on the same or different walls of the installation chamber 20.

In some embodiments, a distribution of the air inlets 25 on the installation chamber 20 (or sections formed by the diaphragm 60 dividing the installation chamber 20, e.g., the first heat dissipation section 21 and/or the second heat dissipation section 22) may be uniform or uneven. For example, the count of the air inlets may be determined based on a density of components and/or heat dissipation. In some embodiments, the installation chamber 20 may be provided with a plurality of air inlets 25 according to the heat dissipation of the one or more detection units 30. A count of air inlet(s) 25 arranged on a unit area of the middle region of the installation chamber 20 may be more than a count of air inlet(s) 25 arranged on a unit area of the side region of the installation chamber 20, thus a density of the air inlet(s) 25 arranged on the middle region may be greater than a density of the air inlet(s) 25 arranged on the side region. Thus, air supplied to the middle region where the heat dissipation of the one or more detection unit 30 is poor may be increased, the heat dissipation efficiency may be improved, the temperature gradient generated by the one or more detection units 30 in different regions may be reduced, and the stability and detection accuracy may be ensured.

The air outlet 26 may be a through hole on the wall of the installation chamber 20. The air outlet 26 may be configured to discharge gas inside the installation chamber 20. In some embodiments, the air outlet 26 may be of any size and shape that meets an actual requirement. For example, the shape of the air outlet may be a circle, a triangle, a square, a polygon, or the like, or any combination thereof. In some embodiments, a count of the air outlet(s) 26 may be one or more. When there is a plurality of air outlets 26, the plurality of air outlets 26 may be arranged on the same or different walls of installation chamber 20.

A position of the outlet air 26 may be determined based on the position of the air inlet 25. In some embodiments, the air outlet 26 may be arranged on a wall of the installation chamber 20 opposite to the air inlet 25. For example, as shown in FIG. 2, the air inlet 25 may be arranged on an upper portion of a first side wall (e.g., the side plane 16 of the housing assembly 10) of the installation chamber 20, and the air outlet 26 may be arranged on a lower portion of a second side wall (e.g., the side plane 14 of the housing assembly 10) opposite to the first side wall. Thus, a path of the air flow may be as long as possible, and the air may flow through as many internal components (e.g., the one or more detection units 30) as possible to take away the heat generated thereby, thereby improving the utilization of the air flow and ensuring the heat dissipation efficiency.

It should be understood that in some other embodiments, the position of the air outlet 26 may be arranged at other positions as required. For example, the air outlet 26 may be arranged on a wall of the installation chamber 20 adjacent to the air inlet 25. For example, the air inlet 25 may be arranged on upper portions of two side walls (e.g., the side plane 14 and the side plane 16 of the housing assembly 10) of the installation chamber 20, and the air outlet 26 may be arranged on a bottom wall (e.g., the second plane 15 of the housing assembly 10) of the installation chamber 20.

In some embodiments, the positions of the air inlet 25 and the air outlet 26 may affect the air flow direction. When the installation chamber 20 is divided into at least two sections, the positions of the air inlet 25 and the air outlet 26 may make air flow directions in adjacent sections different. In some embodiments, the installation chamber 20 may be divided into the first heat dissipation section 21 and the second heat dissipation section 22. As shown in FIG. 3 and FIG. 4, the air inlet 25*a* and the air outlet 26*a* may be arranged on opposite sides of the first heat dissipation section 21 in the direction Y of the one or more detection units 30. The air inlet 25*b* and the air outlet 26*b* may be arranged on opposite sides of the second heat dissipation section 22 in the width direction X of the one or more detection units 30. Thus, by arranging the positions of the air inlet 25 and the air outlet 26, the air of the two sections may be guided to flow in different directions, and the air flow direction in the first heat dissipation section 21 may be perpendicular to the air flow direction in the second heat dissipation section 22.

In some other embodiments, when the installation chamber 20 is divided into at least two sections, the positions of the air inlet 25 and the air outlet 26 may make air flow directions in the two adjacent sections different. In some embodiments, the installation chamber 20 may be divided into the first heat dissipation section 21 and the second heat dissipation section 22, the air inlet 25 (including the air inlets 25*a* and 25*b*) and the air outlet 26 (including the air outlets 26*a* and 26*b*) of each section may be arranged on two opposite sides of the section in the width direction X of the one or more detection units 30. Thus, by arranging the positions of the air inlet 25 and the air outlet 26, the air of the two sections may be guided to flow in the same direction, and the air flow direction in the first heat dissipation section 21 may be parallel to the air flow direction in the second heat dissipation section 22.

In some embodiments, the cooling assembly 40 may include an air guiding assembly 43, and/or an air duct may be formed between the one or more detection units 30 and the installation chamber 20. The air guiding assembly 43 and/or the air duct may directly supply a cooling air flow into a region where the air generated by an air flow generator cannot reach directly in the installation chamber 20*m* thereby enlarging the convection range and/or improving the heat dissipation efficiency. In such cases, the diaphragm 60, the baffle assembly and other components arranged in the installation chamber 20 may be omitted. It should be understood that in some other embodiments, the installation chamber 20 may be provided with one or more diaphragm 60, and the installation chamber 20 may be divided into sections by the one or more diaphragms 60. A portion or all of the sections divided from the installation chamber 20 may cooperate with the air guiding assembly 43 and/or the air duct to enhance the gas convection inside and outside the section(s), thus the heat dissipation efficiency may be improved. More descriptions of the air guiding assembly 43 and the air duct may found elsewhere in the present disclosure, for example, FIG. 7-FIG. 14 and/or the descriptions thereof.

Figure 7:
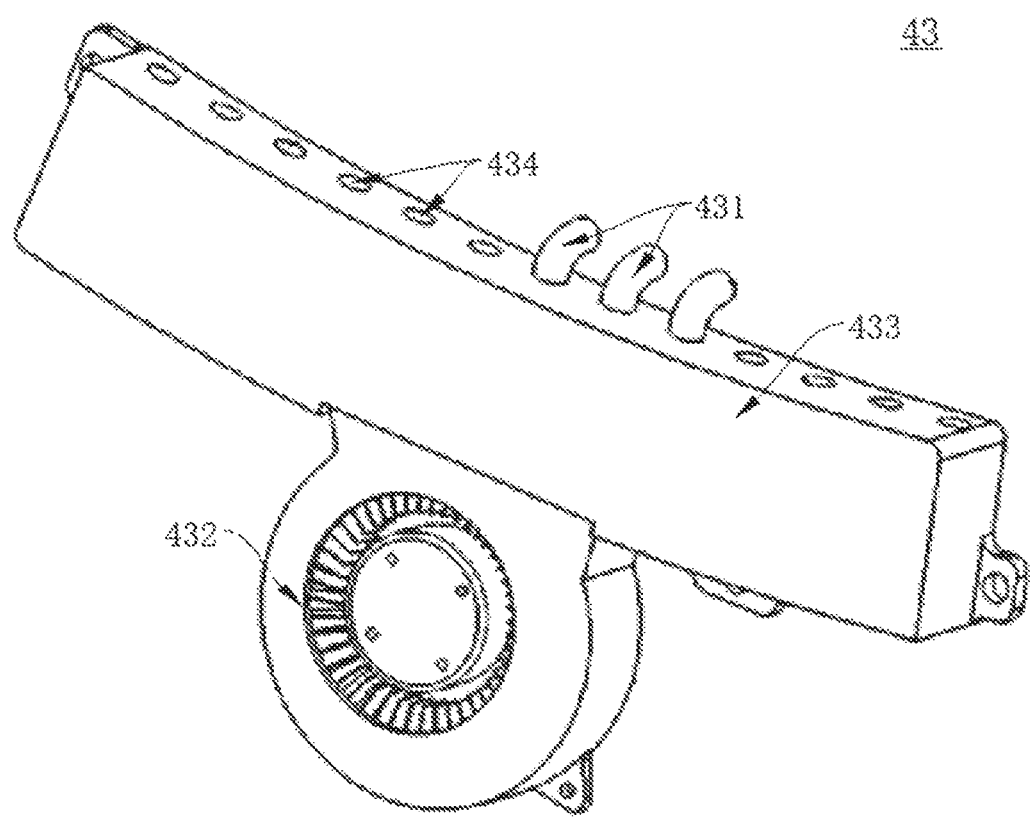
FIG. 7 is a schematic diagram illustrating a structure of an air guiding assembly according to some embodiments of the present disclosure.

FIG. 7 is a schematic diagram illustrating a structure of the air guiding assembly 43 according to some embodiments of the present disclosure. The air guiding assembly 43 may be configured to guide the air flow into the installation chamber 20 (or at least a portion of sections divided from the installation chamber 20, e.g., the first heat dissipation section 21 and/or the second heat dissipation section 22). The heat generated by a component (e.g., the one or more detection units 30) may be taken away by the air guiding assembly 43.

In some embodiments, the air guiding assembly 43 may include one or more air ducts 431. An air duct 431 may be a hollow pipe for guiding the air flow. The air duct 431 may include an inlet end and an outlet end. The outlet end of the air duct 431 may be connected with the air inlet 25 of the installation chamber 20. The inlet end of the air duct 431 may be used for guiding in the air flow. It should be understood that the outlet end of the air duct 431 may be connected with the air inlet 25 of the installation chamber 20, and the arrangement of a position of the outlet end of the air duct 431 may refer to the arrangement of the position of the air inlet 25, which are not be repeated herein.

In some embodiments, the arrangement of the air duct 431 and the air inlet 25 may be determined based on requirements of the heat dissipation. For example, each air inlet 25 may be connected with a corresponding air duct 431. As another example, if the heat dissipation effect in a region is relatively good, the air inlet 25 in the region may not be connected with the air duct 431 to save energy.

In some embodiments, gas may be supplied to the air duct(s) 431 of the air guiding assembly 43 from outside. For example, the air duct(s) 431 may be connected with other air flow generators of the imaging apparatus. In some embodiments, the air guiding assembly 43 may include a device for generating air flow. As shown in FIG. 7, the air guiding assembly 43 may also include a third air device 432. The air flow generated by the third air device 432 may enter the installation chamber 20 through the one or more air ducts 431.

In some embodiments, the third air device 432 may be directly connected with the air duct(s) 431, and the air duct(s) 431 may guide the air flow generated by the third air device 432 directly into the installation chamber 20. In some other embodiments, the air guiding assembly 43 may also include a device for diverting the air flow generated by the third air device 432. As shown in FIG. 7, the air guiding assembly 43 may also include a shunt cover 433 arranged between the third air device 432 and the air duct(s) 431. The shunt cover 433 may be connected with one or more third air devices 432. The shunt cover 433 may be provided with one or more air outlet holes. At least one inlet end of the one or more air ducts 431 may be connected with at least one of the one or more air outlet holes 434.

The shunt cover 433 may be a device for dividing the air flow generated by the third air device 432 into a plurality of sub air flows to ensure that air flow(s) supplied into the air duct(s) 431 connected with the same shunt cover 433 may be uniform. In some embodiments, the shunt cover 433 may be of any shape, such as a sphere or a cuboid with a hollow section inside. The air flow generated by the third air device 432 may fill the section in the shunt cover 433, and the air may flow out of the air outlet hole(s) 434 of the shunt cover 433.

In some embodiments, the one or more air outlet holes 434 on the shunt cover 433 may be arranged on any wall of the shunt cover 433 that does not affect normal releasing of the air flow. In some embodiments, the one or more air outlet holes 434 may be arranged on a side wall of the shunt cover 433 perpendicular to the direction of the air flow generated by the third air device 432. Therefore, the air flow direction in the shunt cover 433 may be a single direction. That is, the air flow generated by the third air device 432 may enter the shunt cover 433 from the air inlet of the shunt cover 433, and then flow to the air outlet hole 434 directly. Thus, the stability and uniformity of the air flow direction may be ensured, and the utilization rate of the air flow may be improved.

In some embodiments, a type and an installation position of the third air device 432 may be determined based on the air flow direction. Merely by way of example, as shown in FIG. 7, the third air device 432 may be a centrifugal air device arranged at a bottom portion of the shunt cover 433. The air outlet hole 434 on the shunt cover 433 may be arranged on a top wall of the shunt cover 433. The gas may enter a space of leaves of the third air device from an axial direction of the third air device. A high-speed air flow formed by rotating and pressurizing the gas may leave the leaves in a radial direction. The air flow may be flowed from the bottom to the top of the shunt cover 433. The flow direction of the air flow in the shunt cover 433 may be from bottom to top. It should be understood that in some other embodiments, the third air device 432 may be designed as other types of air devices and be arranged on other positions based on the requirement of the air flow direction. For example, the third air device 432 may be an axial air device. The air flow generated by the axial air device may flow along an axial direction of leaves of the axial air device. The axial air device may be arranged on a wall of the shunt cover 433 opposite to the air outlet hole 434.

In some embodiments, a position of the air outlet hole 434 on the shunt cover 433 may be determined based on the position of the air inlet 25 of the installation chamber 20, and each air outlet hole 434 may correspond to an air inlet 25.

In some embodiments, the air outlet hole 434 and the air inlet 25 may be evenly or unevenly distributed. For example, for regions with poor heat dissipation, more air inlets 25 and corresponding air outlet holes 434 may be provided to improve the effect of air cooling. In some embodiments, between each pair of air outlet holes 434 and air inlets 25, the air duct 431 may be provided for communication based on the requirements of heat dissipation, or the air duct 431 may not be provided. In some embodiments, each air outlet hole 434 may be connected with the nearest air inlet 25 through the air duct 431, or may be connected with any other air inlet 25 through an extended air duct 431.

In some embodiments, a count of the air guiding assembly 43 may be one or more. In some embodiments, the installation chamber 20 may be divided into a plurality of regions based on the heat dissipation, the density of the components, or the like. For example, along the direction Y of the one or more detection units 30, the installation chamber 20 may be divided into a middle region and side regions of the middle region. A plurality of air guiding assemblies 43 may be respectively connected with the air inlets 25 of the installation chamber 20 in different regions to dissipate heat in the different regions. In some embodiments, a count of the air duct(s) and a count of the third air device(s) 432 of each air guiding assembly 43 may be determined based on the heat dissipation of the different regions and the density of components of the installation chamber 20 connected to the air guiding assembly 43. For example, the air guiding assembly 43 connected with the side regions may be provided with a third air device 432. The air guiding assembly 43 connected with the middle region may be provided with two, three, or four third air devices 432 to increase the air supplied to the middle region of the installation chamber 20.

Figure 8:
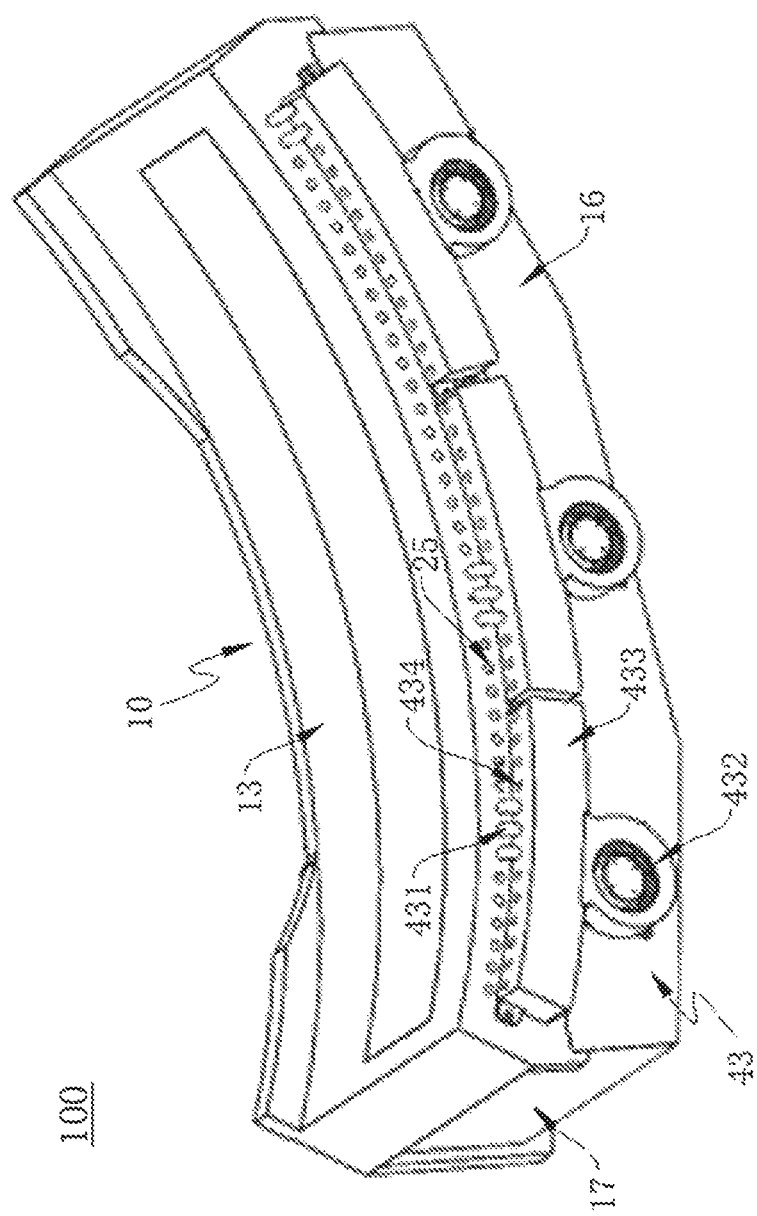
FIG. 8 is a schematic diagram illustrating an installation structure of an air guiding assembly according to some embodiments of the present disclosure.

FIG. 8 is a schematic diagram illustrating an installation structure of an air guiding assembly 43 according to some embodiments of the present disclosure. As shown in FIG. 8, the air guiding assembly 43 may be arranged on the side wall of the installation chamber 20, which may be simple to install. Besides, a small space may be occupied, and the imaging of the imaging apparatus may not be affected. In some embodiments, the air guiding assembly 43 may be arranged on the side wall of the installation chamber 20 corresponding to the one or more detection units 30 to facilitate air supply to the one or more detection units 30. For example, the one or more detection units 30 may be arranged on the left side wall (e.g., the side plane 16 of the housing assembly 10) in the installation chamber 20, and the air guiding assembly 43 may be arranged on the outside of the left side wall (e.g., the side plane 16 of the housing assembly 10). In some embodiments, the air guiding assembly 43 may be arranged on other components (e.g., a rotating gantry) of the imaging apparatus, and the air outlet hole 434 of the shunt cover 433 may be connected with the air inlet 25 of the installation chamber 20 through a long air duct 431. It should be understood that in other embodiments, the outlet end and inlet end of the air duct 431 may be directly connected with the third air device 432 and the air inlet 25 of the installation chamber 20, respectively.

In some embodiments, a plurality of air guiding assemblies 43 may be arranged on a side wall of the installation chamber 20 as shown in FIG. 8. Additionally or alternatively, a single air guiding assembly 43 may be arranged on the side wall of the installation chamber 20, and a length of the shunt cover 433 of the air guiding assembly 43 may be a sum of lengths of the three shunt covers 433 shown in FIG. 8.

In addition to the connection with the air inlet 25 of the installation chamber 20, in some other embodiments, the air guiding assembly 43 may be connected with the air outlet 26 of the installation chamber 20. It should be understood that a manner of cooperation and arrangement of the air guiding assembly 43 and the air outlet 26 of the installation chamber 20 may be similar to a manner of cooperation and arrangement of the air guiding assembly 43 and the air inlet 25 of the installation chamber 20. More descriptions may be found in FIG. 7 and FIG. 8, which are not repeated herein.

In some embodiments, when the installation chamber 20 is divided by one or more diaphragms 60 into at least two sections, the air guiding assembly 43 may cooperate with a portion or all of the at least two sections for dissipating heat. In some embodiments, a single air guiding assembly 43 may be configured to cool and dissipate heat from multiple sections. For example, the detection apparatus 100 may be provided with a single air guiding assembly 43. The air inlet 25 of each section may be connected with a portion of a plurality of air ducts 431 of the air guiding assembly 43. The air flow generated by the third air device 432 may be supplied to the multiple sections through the shunt cover and the air ducts. In some other embodiments, the detection apparatus 100 may provide one or more air guiding assemblies 43 for cooling and heat dissipation for each section. For example, the air inlet 25 of each section may be connected with all air ducts 431 of a corresponding air guiding assembly 43. The air flow in each section may be supplied by the third air device 432 of the corresponding air guiding assembly 43. The manner of the cooperation of the air guiding assembly 43 and the sections divided from the installation chamber 20 by the diaphragm(s) 60 may similar to the manner of the cooperation and the arrangement of the air guiding assembly 43 and the installation chamber 20. More descriptions may be found in FIG. 7 and FIG. 8, which are not repeated herein.

Figure 9:
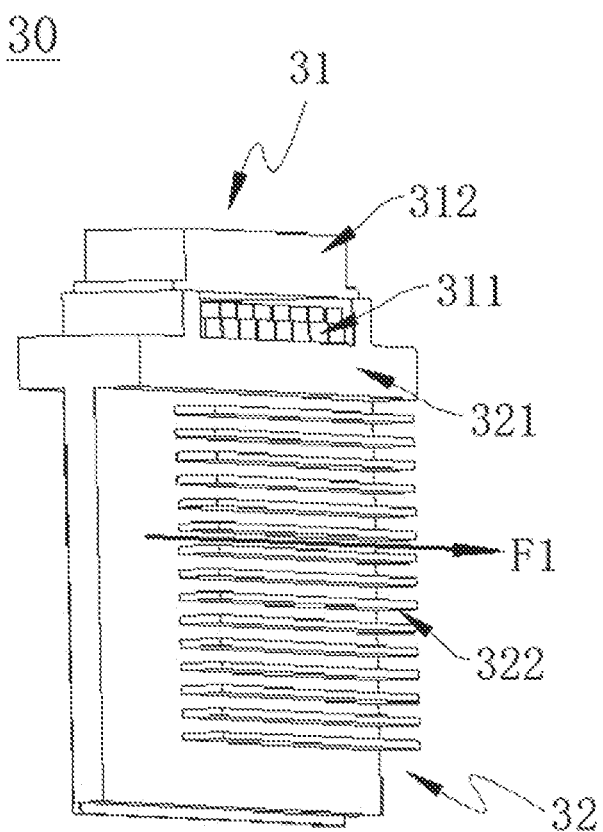
FIG. 9 is a schematic diagram illustrating a structure of a detection unit according to some embodiments of the present disclosure.

FIG. 9 is a schematic diagram illustrating a structure of the detection unit 30 according to some embodiments of the present disclosure.

In some embodiments, the detection assembly 31 of the detection unit 30 may include the detection module 311. A count of the detection module 311 may be one or more, and the one or more detection modules 311 may be disassembled or assembled to form the detection assembly 31. The count of the detection module 311 may be fixed or adjustable based on different requirements, e.g., a required resolution of an image, a required size of the image, a size of an object, or the like, or any combination thereof.

As shown in FIG. 4 and FIG. 9, in some embodiments, when there is a plurality of detection modules 311, the plurality of detection modules 311 may be arranged in parallel along an axial direction (i.e., the width direction X of the one or more detection units 30) of a detection space. It should be understood that the plurality of detection modules 311 may not be limited to be arranged along the axial direction of the detection space in the above embodiments. In some other embodiments, the plurality of detection modules 311 may also be arranged in other directions, as long as the plurality of detection modules 311 cooperate with each other to perform the signal recipient and signal conversion function. In some embodiments, the plurality of detection modules 311 may be made of LSO crystal. It should be understood that in some other embodiments, the plurality of detection modules 311 may be made of BaF2, NaI, or other types of crystals. The detection module 311 may have any suitable shape. For example, the detection module 311 may have a flat shape, a curved shape, a circular shape, or the like, or any combination thereof.

As shown in FIG. 9, in some embodiments, the detection assembly 31 may also include an anti-scatter grid 312. The anti-scatter grid 312 may absorb a scattered ray. Types of the ray may include, for example, an electromagnetic ray, a particle ray, or the like. The anti-scatter grid 312 may be made of a high absorbent material capable of absorbing one or more types of rays. For example, the high absorbent material may include tungsten, lead, uranium, gold, silver, copper, molybdenum, or the like. The anti-scatter grid 312 may also be made of a low absorbent material that allows one or more types of rays to pass through. For example, the low absorbent material may allow substantially all rays to pass through the material. As another example, the low absorption material may merely absorb certain rays. For example, all amount or a certain amount of rays on the low absorbent material may pass through the material. The low absorbent material may include a resin, a fiber material, a rubber, an inorganic non-metallic material (such as ceramics), or the like. The high absorbent material and the low absorbent material may absorb different amounts of rays. For example, the high absorbent material may absorb more rays than the low absorbent material. The high absorbent material and/or the low absorbent material may be placed in the anti-scattering grid 312 to absorb the scattered ray.

Figure 10:
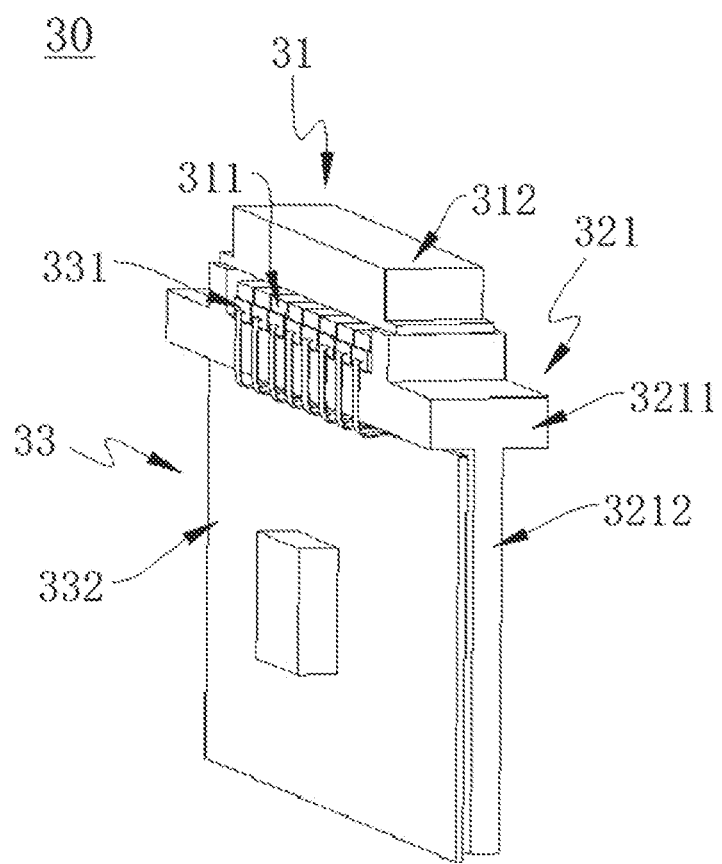
FIG. 10 is a schematic diagram illustrating a structure of a detection unit according to some embodiments of the present disclosure.

FIG. 10 is a schematic diagram illustrating a structure of the detection unit 30 according to some embodiments of the present disclosure.

As shown in FIG. 10, in some embodiments, the circuit board assembly 33 may include a first circuit board module 331. A photomultiplier tube may be arranged in the first circuit board module 331. The first circuit board module 331 may be electrically connected with the detection module 311 in the detection assembly 31. The first circuit board module 331 and the detection module 311 may be in thermal contact. The first circuit board module 331 may be configured to convert a detection signal obtained by the detection module 311 into an electrical signal.

In some embodiments, the circuit board assembly 33 may also include a second circuit board module 332. The second circuit board module 332 may be provided with a processing chip. The second circuit board module 332 may be electrically connected with the first circuit board module 331. The second circuit board module 332 may preprocess the electrical signal converted by the first circuit board module 331 and transmit the preprocessed electrical signal to an external signal processing device. The external signal processing device may receive the preprocessed electrical signal and construct a functional image containing physiological information of an object based on the preprocessed electrical signal.

In some embodiments, the first circuit board module 331 and the second circuit board module 332 may be arranged on the same circuit board or on different circuit boards. A connection form of the circuit board modules may be determined based on an actual requirement.

When the installation chamber 20 is divided into at least two sections along the height direction Z of the one or more detection units 30, different components of the circuit board assembly 33 (e.g., the first circuit board module 331 and the second circuit board module 332) may be accommodated and fixed in different sections. In some embodiments, the installation chamber 20 may be divided into the first heat dissipation section 21 and the second heat dissipation section 22 along the height direction Z of the one or more detection units 30. The first circuit board module 331 of each detection unit 30 may be accommodated and fixed in the first heat dissipation section 21, and the second circuit board module 332 of each detection unit 30 may be accommodated and fixed in the second heat dissipation section 22. Compared to the second circuit board module 332, the first circuit board module 331 may have a relatively high lightproof requirement and be more sensitive to temperature. The first circuit board module 331 and the second circuit board module 332 may be arranged in different sections for cooling and dissipating heat. At the same time, the structure of each section may be arranged based on lightproof requirements of different components, taking the heat dissipation efficiency and the working stability of the detection apparatus 100 into account.

In some embodiments, the heat dissipation assembly 32 may include a support 321. The support 321 may be in thermal contact with the detection assembly 31 and/or the circuit board assembly 33. The support 321 may be configured to transfer and dissipate heat from other components (e.g., the detection assembly 31 and/or the circuit board assembly 33) of the one or more detection units 30. In some embodiments, as shown in FIG. 4, different supports 321 of different detection units 30 may be connected with each other, and arranged in intervals. for example, the supports 321 of any two adjacent detection units 30 may be connected with each other by way of bonding, adhesive, welding, fastener, or the like, or any combination thereof. In some embodiments, different detection units 30 may be arranged on a wall of the installation chamber 20 through the supports 321, e.g., arranged on a top wall, a side wall, etc., f the installation chamber 20.

In some embodiments, the air flow in the installation chamber 20 may flow in a direction parallel to a main heat dissipation plane of the support 321 to reduce wind resistance and improve heat dissipation efficiency. It should be noted that "main heat dissipation plane" may refer to a plane whose area accounts for more than a predetermined value of a superficial area of the support 321, such as more than 20%, 30% or 40%.

As shown in FIG. 10, in some embodiments, the support 321 may include a diaphragm part 3211 and a heat dissipation diaphragm 3212 fixed to each other. The diaphragm part 3211 and the heat dissipation diaphragm 3212 may form a support 321 of a T-shaped sectional view. It should be understood that in some other embodiments, the structure of the support 321 may be designated as other shapes. For example, the sectional view of the support 321 may have an L shape, a rectangular shape, a trapezoidal shape, a polygonal shape or any other regular or irregular shapes, as long as the thermal contact of the support 321 and the detection assembly 31 and/or the circuit board assembly 33 may be implemented.

Heat transfer may be implemented between the diaphragm part 3211 and the circuit board assembly 33 and/or the detection assembly 31. For heat transferred to the diaphragm part 3211, a portion of the heat may be directly released to the periphery, and a portion of the heat may be transferred to the heat dissipation diaphragm 3212. In some embodiments, the diaphragm part 3211 and the first circuit board module 331 and/or the detection assembly 31 may be in thermal contact. In some embodiments, the diaphragm part 3211 may be opened with one or more heat dissipation grooves on a portion of a surface of the diaphragm part 3211, e.g., a surface adjacent to a connecting surface of the diaphragm part 3211 and the heat dissipation diaphragm 3212, thus the heat dissipation area may be increased.

The heat dissipation diaphragm 3212 may transfer heat transfer among the diaphragm part 3211 and/or the second circuit board module 332. The heat transferred to the heat dissipation plate 3212 may be directly released to the periphery, or the heat may also be transferred to other heat dissipation structures. In some embodiments, the heat dissipation diaphragm 3212 may be connected with a side of the diaphragm part 3211 away from the first circuit board module 331 and/or the detection assembly 31. The heat dissipation diaphragm 3212 may extend in a direction away from the first circuit board module 331 and/or the detection assembly 31. The heat dissipation diaphragm 3212 may be in thermal contact with the second circuit board module 332.

In some embodiments, since the plurality of supports 321 may be arranged along the direction Y of the one or more detection units, similar to the arc arrangement of the detection assembly 31, the plurality of heat dissipation diaphragms 3212 may be arranged radially along the direction Y of the one or more detection units. It should be understood that the arrangement of the heat dissipation diaphragm 3212 may be determined based on an actual requirement.

In some embodiments, the heat dissipation assembly 32 may also include a heat dissipation structure arranged on the support 321. The heat dissipation structure may include a plurality of heat dissipation fins 322. As shown in FIG. 10, the plurality of heat dissipation fins 322 may be arranged side by side with intervals on the heat dissipation diaphragm 3212. The heat dissipation fin 322 may have any suitable shape and/or size. For example, a sectional view of the heat dissipation fin 322 may have a rectangular shape, a trapezoidal shape, a polygonal shape, or any other regular or irregular shapes. In some embodiments, the plurality of heat dissipation fins 322 may be parallel and/or substantially parallel to each other. The "substantially parallel" may refer to that an angle between two of the plurality heat dissipation fins 322 may be close to zero, for example, smaller than 60°, smaller than 50°, smaller than 40°, smaller than 30°, smaller than 20°, smaller than 10°, or smaller than 5°.

The direction of the heat dissipation fins 322 may be determined based on the flow direction of the air flow in the installation chamber 20. In some embodiments, in the installation chamber 20 where the heat dissipation fin 322 is located or in a section formed by dividing the installation chamber 20 by the diaphragm 60, an extension direction of the heat dissipation fin 322 may be parallel or substantially parallel to the flow direction of the air flow supplied by the cooling assembly 40 to the heat dissipation fin 322. It should be noted that the "substantially parallel" may refer to that on at least a portion of the flow path of the air flow, an angle between the extension direction of the heat dissipation fin 322 and the flow direction of the air flow may be close to zero, for example smaller than 20°, smaller than 15°, smaller than 10° or smaller than 5°.

As shown in FIG. 4 and FIG. 10, in some embodiments, when the installation chamber 20 is divided into the first heat dissipation section 21 and the second heat dissipation section 22 by the first diaphragm 61, the air flow generated by the second air assembly 42 in the second heat dissipation section 22 may flow in a direction parallel to A main heat dissipation plane (such as a surface of the heat dissipation diaphragm 3212) of the support 321. The heat dissipation fin 322 may be accommodated and fixed in the second heat dissipation section 22 with the heat dissipation diaphragm 3212 of the support 321. An extension direction of the heat dissipation fin 322 may be parallel to an air supply direction F1 of the second air assembly 42. By such arrangement, heat dissipation space(s) may be formed between each of the plurality of heat dissipation fins 322 on the heat dissipation diaphragm 3212 and formed between a heat dissipation diaphragm 3212 and another heat dissipation diaphragm 3212. The air flow may be flow through the heat dissipation space(s), so as to facilitate the heat dissipation of the heat dissipation diaphragm 3212.

In some embodiments, the plurality of heat dissipation fins 322 may cooperate with the air duct structure arranged in the installation chamber 20 to improve the heat dissipation efficiency. More descriptions of the heat dissipation fin 332 may be found in FIG. 13 and FIG. 14 and/or the descriptions thereof.

When the installation chamber 20 is divided into at least two sections along the height direction Z of the one or more detection units 30, different components of the heat dissipation assembly 32 may be accommodated and fixed in different sections. In some embodiments, the installation chamber 20 may be divided into the first heat dissipation section 21 and the second heat dissipation section 22 by the first diaphragm 61 along the height direction Z of the one or more detection units 30. The heat dissipation assembly 32 may be in thermal contact with the detection assembly 31 located in the first heat dissipation section 21, and at least a portion of the heat dissipation assembly 32 may extend to the second heat dissipation section 22. The support 321 may extend from the first heat dissipation section 21 to the second heat dissipation section 22. The diaphragm part 3211 of the support 321 may be arranged in the connection between the first heat dissipation section 21 and the second heat dissipation section 22. The diaphragm part 3211 may cooperate with the first diaphragm 61 to divide the installation chamber 20 into the first heat dissipation section 21 and the second heat dissipation section 22. The heat dissipation diaphragm 3212 of the support 321 may extend in the second heat dissipation section 22 along a direction away from the detection assembly 31 and/or the first circuit board module 331. A plurality of heat dissipation fins 322 may be arranged side by side with intervals on the heat dissipation diaphragm 3212.

In some embodiments, the heat dissipation assembly 32 may be integrally formed to reduce the resistance of heat transfer between connection interfaces of the components in the heat dissipation assembly 32. At the same time, the support 321 may be integrally formed, thus the convenience of installation may be improved. The support 321 may be made of a heat conducting material, such as copper, aluminum, or the like. It should be understood that in some other embodiments, the heat dissipation assembly 32 may be formed by other molding methods as required, such as welding, molding, etc.

In some embodiments, the heat dissipation assembly 32 may be arranged corresponding to the detection assembly 31 and/or the circuit board assembly 33 of each detection unit 30. Thus, heat generated by the detection assembly 31 and/or the circuit board assembly 33 of each detection unit 30 may be effectively conducted and released. Moreover, the air flow generated by the cooling assembly 40 may flow through the heat dissipation space(S) formed between the plurality of heat dissipation diaphragms 3212, thus the heat may be effectively discharged from the installation chamber 20 or the sections formed by dividing the installation chamber 20 by the diaphragm 60.

It should be understood that in some other embodiments, the detection unit(s) 30 may not be provided with the heat dissipation assembly 32. Other structures may support the detection unit(s) 30, such as setting a support frame, as long as the detection unit(s) 30 implements the function of signal detection and processing.

In some embodiments, the detection unit(s) 30 may include a windshield 34. The windshield 34 may be arranged on one side or two opposite sides of the detection unit(s) to guide/block the air flow to enhance the heat dissipation of the detection unit(s) 30. More descriptions of the windshield 34 may be found in FIG. 11 and FIG. 12 and/or the descriptions thereof.

Figure 11:
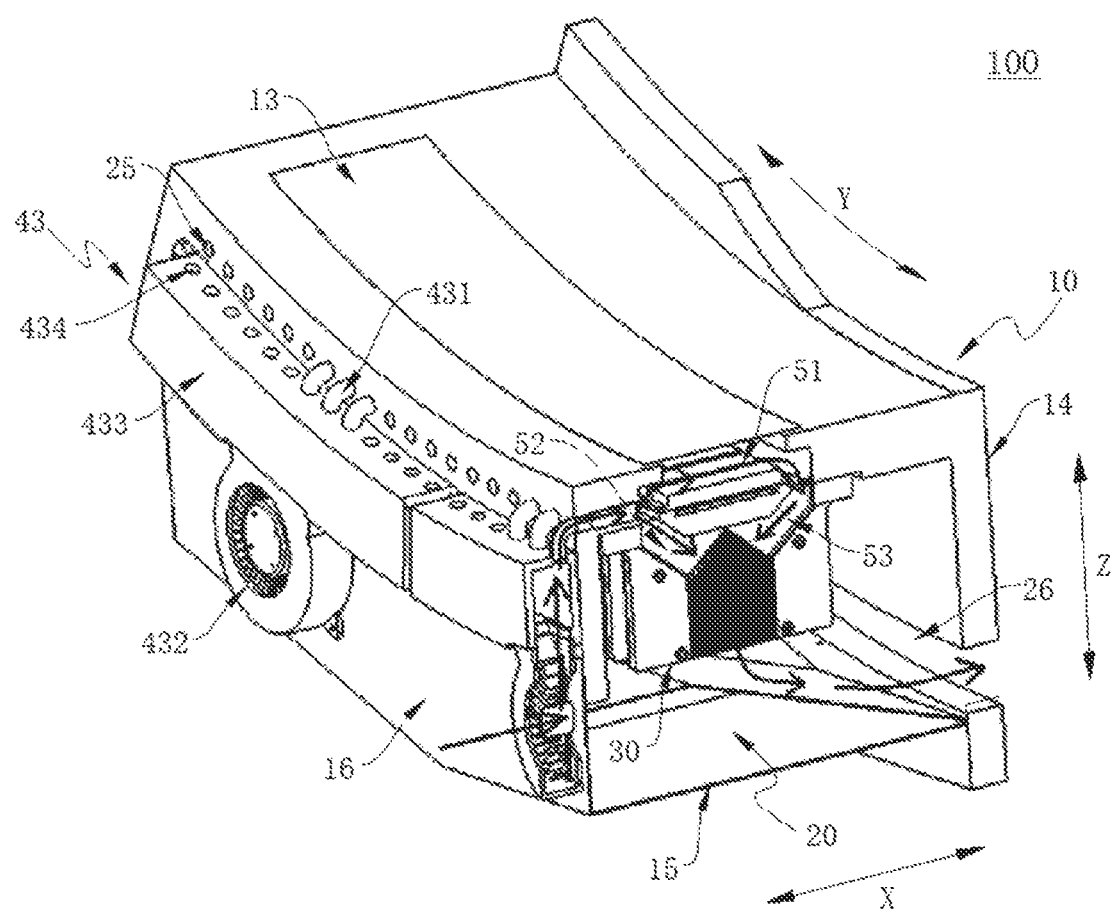
FIG. 11 is a schematic diagram illustrating a structure of an air duct and an air flow direction according to some embodiments of the present disclosure.
Figure 12:
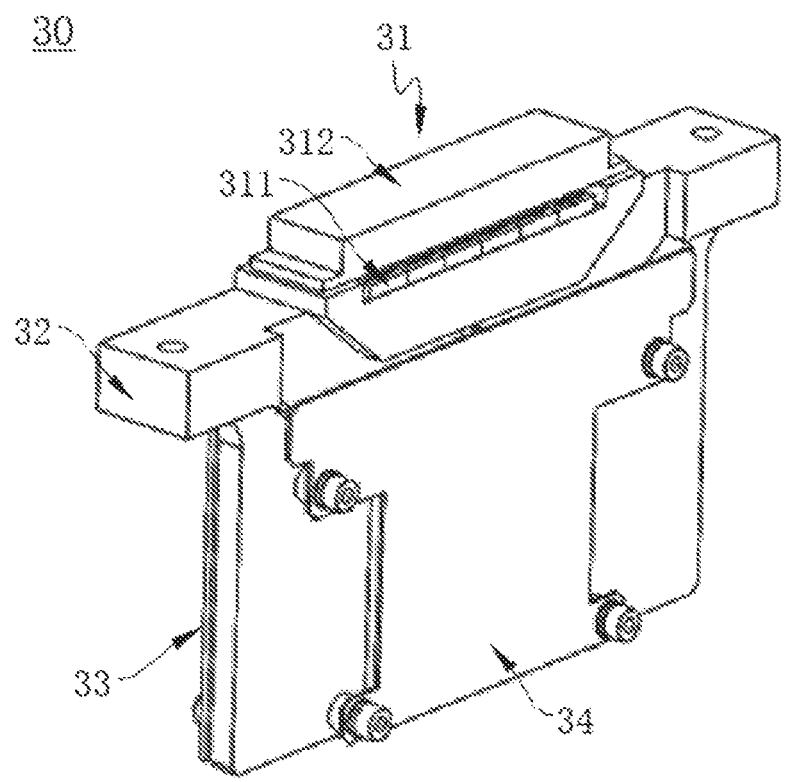
FIG. 12 is a schematic diagram illustrating a structure of a detection unit with an air duct according to some embodiments of the present disclosure.

FIG. 11 is a schematic diagram illustrating a structure of an air duct and an air flow direction according to some embodiments of the present disclosure. FIG. 12 is a schematic diagram illustrating a structure of the detection unit 30 with an air duct according to some embodiments of the present disclosure. As shown in FIG. 11, a first air duct 51 may be formed between the one or more detection units 30 and a top wall (e.g., the first side plane 13 of the housing assembly 10) of the installation chamber 20. A second air duct 52 and a third air duct 53 passing through the detection unit 30 may be arranged on one side of the one or more detection units 30. The first air duct 51 and the second air duct 52 may be both connected with the air inlet 25. The third air duct 53 may be connected with the first air duct 51. The second air duct 52 and the third air duct 53 may be both connected with the air outlet 26.

The first air duct 51, the second air duct 52 and the third air duct 53 may be channels for guiding gas flow. The first air duct 51 may be arranged above the one or more detection units 30. The second air duct 52 and the third air duct 53 may be arranged on the same side of the one or more detection units 30. Merely by way of example, for a detection unit 30 of a flat shape, the detection unit 30 may have two opposite side planes with the largest areas, and the areas of the two side planes may be equal. The second air duct 52 and the third air duct 53 may be arranged on one of the two opposite side planes. At the same time, the one of the two opposite side planes may be opposite to a side plane of an adjacent detection unit 30. In some embodiments, the first air duct 51 may be a gap between the detection unit 30 and the top wall of the installation chamber 20. In some embodiments, the second air duct 52 and the third air duct 53 may be grooves passing through the detection unit 30 from up to down. Merely by way of example, two grooves may be arranged on one side plane of the detection unit 30, and each groove may pass through the side plane of the detection unit 30, respectively. In some embodiments, the two grooves may be parallel and/or substantially parallel to each other. The "substantially parallel" may refer to that an angle between the two grooves is close to zero, for example, smaller than 60°, smaller than 50°, smaller than 40°, smaller than 30°, smaller than 20°, smaller than 10°, or smaller than 5°. In some embodiments, the windshield 34 may be arranged to cover the two grooves. The windshield 34 may cover a portion or all of the two grooves, so that a portion or all of the grooves may form a through-hole shape, so as to control the air flow direction. Thus, the heat on the surface of the detection unit 30 may be taken away to the greatest extent. In some embodiments, the second air duct 52 and the third air duct 53 may be hole channels passing through the one or more detection units 30 from up to down. Merely by way of example, two through holes may be arranged on one side plane of the one or more detection units 30, and each through hole may pass through the side plane of the one or more detection units 30, respectively. The two through holes may be parallel and/or substantially parallel to each other, and the air flow may flow through the two through holes, taking away the heat of the one or more detection units 30.

In some embodiments, the air flow may be supplied from the air inlet 25 to the installation chamber 20. The air flow may be divided into two air flows, entering the first air duct 51 and the second air duct 52, respectively. The sub air flow in the first air duct 51 may then enter the third air duct 53 and be finally released through the air outlet 26. The sub air flow in the second air duct 52 may be released through the air outlet 26. The airflow from the air inlet 25 may flow through the first air duct 51, the second air duct 52, and the third air duct 53 and take away both heat Q1 transmitted by the heat conduction of the detection module(s) 311 and heat Q2 inside the sections, ensuring the stability of the working environment temperature of the detection module(s) 311 and further ensuring the image quality.

Figure 13:
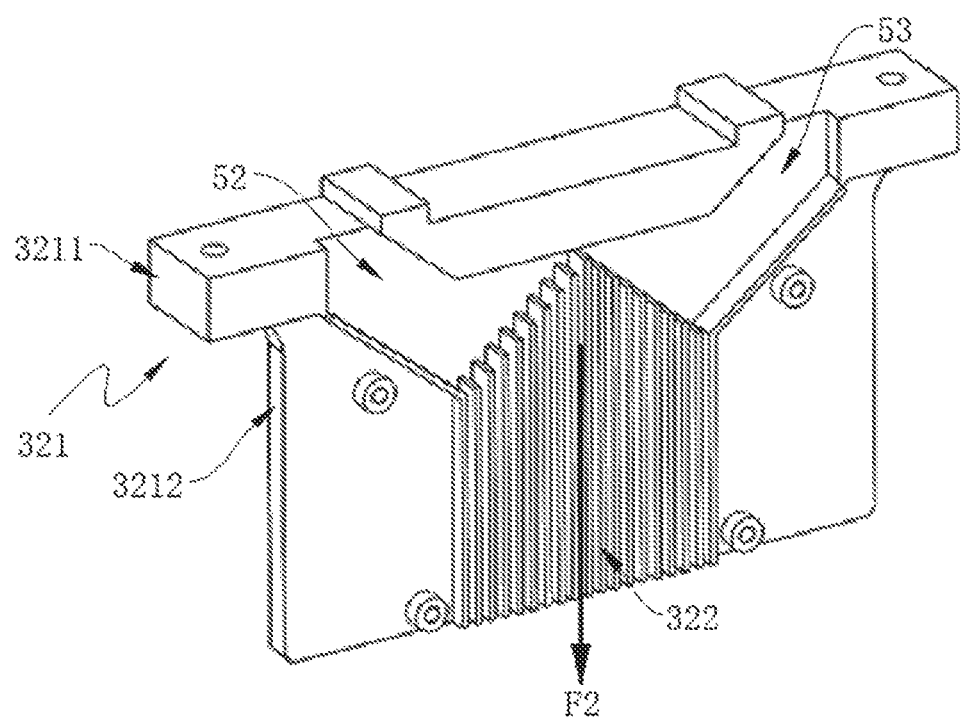
FIG. 13 is a schematic diagram illustrating a structure of an air duct according to some embodiments of the present disclosure.

FIG. 12 is a schematic diagram illustrating a structure of the detection unit 30 with an air duct according to some embodiments of the present disclosure. FIG. 13 is a schematic diagram illustrating a structure of an air duct according to some embodiments of the present disclosure. As shown in FIG. 13, in some embodiments, the second air duct 52 and the third air duct 53 may be provided with heat dissipation fins 322. The heat dissipation fins 322 may be fixed on a surface of the one or more detection units 30 to increase the heat dissipation area and improve the heat dissipation efficiency. In some embodiments, the heat dissipation fins 322 may be arranged along the air flow direction in the air duct, thus the air flow may be divided into a plurality of air flows. As shown in FIG. 11 and FIG. 13, the air duct may guide the air flow generated by the third air device 432 to flow through the heat dissipation diaphragm 3212 and the heat dissipation fin 322 along the height direction Z of the one or more detection units 30. An extension direction of the heat dissipation fin 322 may be substantially parallel to a supply direction F2 of the air flow of the third air device 432.

Figure 14:
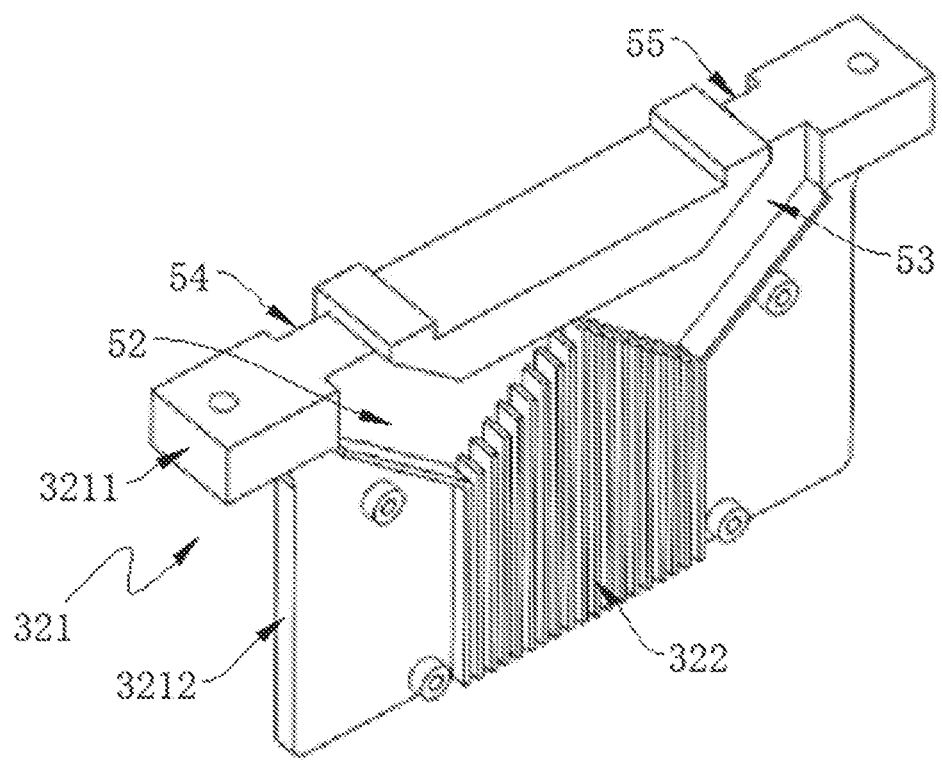
FIG. 14 is a schematic diagram illustrating a structure of an air duct according to some embodiments of the present disclosure.

FIG. 14 is a schematic diagram illustrating a structure of an air duct according to some embodiments of the present disclosure. As shown in FIG. 14, another side of the one or more detection units 30 may be provided with a fourth air duct 54 and/or a fifth air duct 55 passing through the one or more detection units 30. The fourth air duct 54 may be connected with the air inlet 25. The fifth air duct 55 may be connected with the first air duct 51. The fourth air duct 54 and/or the fifth air duct 55 may be connected with the air outlet 26.

The fourth air duct 54 and the fifth air duct 55 may be channels for guiding gas flow. The fourth air duct 54 and the fifth air duct 55 may be arranged on the same side of the one or more detection units 30, and the same side may refer to the opposite side of a side provided with the second air duct 52 and the third air duct 53. In some embodiments, only the fourth air duct 54 or only the fifth air duct 55 may be provided, or both the fourth air duct 54 and the fifth air duct 55 may be provided. In some embodiments, the fourth air duct 54 may be arranged at a position corresponding to the second air duct 52, and have a similar structure to the second air duct 52. In some embodiments, the fifth air duct 55 may be arranged at a position corresponding to the third air duct 53, and have a similar structure to the third air duct 53.

In some embodiments, the air flow may be supplied from the air inlet 25 to the installation chamber 20, and be divided into three air flows. The three air flows may be supplied to the first air duct 51, the second air duct 52 and the fourth air duct 54, respectively. The air flow in the first air duct 51 may be then divided into two air flows, which may enter the third air duct 53 and the fifth air duct 55, respectively, and finally may be released through the air outlet 26. The air flow in the second air duct 52 and the fourth air duct 54 may be released through the air outlet 26. The air flow from the air inlet 25 may pass through the first air duct 51, the second air duct 52, the third air duct 53, the fourth air duct 54, and the fifth air duct 55, respectively, and both two side planes of the detection unit 30 by air.

In some embodiments, for the sections in the installation chamber 20, the cooling performance parameters of the cooling assembly 40 acting on each section may be different. Thus, the effect of temperature control on different sections may be ensured. It should be noted that the cooling performance parameters may be parameters related to the temperature control of the detection apparatus 100. The cooling performance parameters may be selected from at least one of the following feature parameters: a count of air ducts 431/air inlets 25 corresponding to a section, the count of air devices, and a speed of a air device.

In some embodiments, when at least two sections divided from the installation chamber 20 are arranged along the direction Y of the one or more detection units 30, the cooling performance parameters of the cooling assembly acting on a section in the middle position may be greater than the cooling performance parameters of the cooling assembly acting on a section in a side position. For example, among one or more feature parameters contained in the cooling performance parameters, a portion or all of the feature parameter(s) of the section in the middle position may be higher than the corresponding feature parameters of the section in the side position. For example, the count of air devices corresponding to the section in the middle position may be the same as the count of air devices corresponding to the section in the side position. A speed of the air devices and a count of the air inlets of the section in the middle may be higher than a speed of the air devices and a count of the air inlets of the section in the side position. In terms of the distribution density and heat dissipation difficulty of the one or more detection units 30 and other components contained in the section, the section in the middle position may be higher than the section in the side position. Thus, the larger cooling performance parameters may be provided to allow the section in the middle position to supply more air flows, and the cooling effect may be better, thus the temperature gradient between the detection unit(s) 30 in different regions may be avoided.

In some embodiments, when at least two sections divided from the installation chamber 20 are arranged along the height direction Z of the one or more detection units 30, the cooling performance parameters of the cooling assembly acting on a section at an upper end position may be greater than the cooling performance parameters of the cooling assembly acting on a section at a lower end position. For example, as shown in FIG. 3, the first heat dissipation section 21 may be located above the second heat dissipation section 22. Compared to components (e.g., the second circuit board module 332, etc.) contained in the second heat dissipation section 22 of each detection unit 30, components (e.g., the detection module 311, the first circuit board module 331, etc.) contained in the first heat dissipation section 21 of each detection unit 30 may be more sensitive to light and a temperature condition. The temperature fluctuation may affect the stability and imaging quality of the one or more detection units 30. The first heat dissipation section 21 may be provided with larger cooling performance parameters to supply more air flows, thus the cooling effect may be better, and the occurrence of the above problems may be avoided.

In some embodiments, the detection apparatus 100 may include one or more temperature sensors arranged in different sections divided from the installation chamber 20. The one or more temperature sensors may be configured to detect the temperature of a corresponding section. Further, the detection apparatus 100 may be provided with a control unit. The control unit may be electrically connected with components, e.g., the one or more temperature sensors, air devices or other components. The control unit may obtain the temperature of the section detected by the temperature sensor(s), and adjust the cooling performance parameters of the cooling assembly 40 acting on each section based on the temperature of each section. It should be understood that the control unit may be omitted from the detection apparatus 100, and the cooling performance parameters of the cooling assembly 40 acting on each section may be adjusted in real-time or periodically based on the temperature of each section through a control device of the imaging apparatus, as long as the purpose of temperature control of the sections is achieved.

In some embodiments, for the installation chamber 20, or the sections formed by the diaphragm 60 dividing the installation chamber 20 along the height direction Z of the one or more detection units 30, different regions may be divided based on a density/heat dissipation of various component contained in the installation chamber 20 or the sections. Thus, the cooling performance parameters of the cooling assembly 40 acting on different regions may be different, the effect of temperature control in different regions may be ensured. The cooling performance parameters may be selected from at least one of the following feature parameters: the count of air ducts 431/air inlets 25 corresponding to a region, the count of air devices, and the speed of the air devices. For example, the installation chamber 20 shown in FIG. 11 may be divided into a middle region and two side regions of the middle region along the direction Y of the one or more detection units 30. As shown in FIG. 3, the first heat dissipation section 21 may be divided into a middle region and two side regions along the direction Y of the one or more detection units 30. The density/heat dissipation difficulty of the components in the middle region may be higher than that in the side regions.

In some embodiments, the detection apparatus 100 may control temperature in different regions by providing different cooling performance parameters for different regions. For example, the cooling performance parameters of the cooling assembly 40 acting on the middle region of the installation chamber 20 may be greater than the cooling performance parameters of the cooling assembly 40 acting on the side regions of the installation chamber 20. Thus, more air flows may be supplied to the middle region, and the temperature gradient between the one or more detection units 30 in different regions may be reduced.

In some embodiments, the detection apparatus 100 may include one or more temperature sensors arranged in different regions. The one or more temperature sensors may be configured to detect the temperature of a corresponding region. Further, the detection apparatus 100 may be provided with a control unit. The control unit may be electrically connected with components, e.g., the one or more temperature sensor, air device, or other components. The control unit may obtain the temperature of the corresponding region detected by the temperature sensor(s), and the cooling performance parameters of the cooling assembly 40 acting on the corresponding region may be adjusted based on the temperature of the corresponding region. It should be understood that the control unit may be omitted from the detection apparatus 100. The detection apparatus 100 may also adjust the cooling performance parameters of the cooling assembly 40 acting on a region based on the temperature through a control device of the imaging apparatus, as long as the purpose of temperature control is achieved.

It should be understood that in some other embodiments, the detection apparatus 100 may simultaneously control temperature in different sections and different regions. For example, as shown in FIG. 3, the detection apparatus 100 may control temperatures in the first heat dissipation section 21 and the second heat dissipation section 22, respectively. On this basis, the temperature in the first heat dissipation section 21 may be controlled based on different regions, thus the heat dissipation efficiency may be further optimized.

Figure 15:
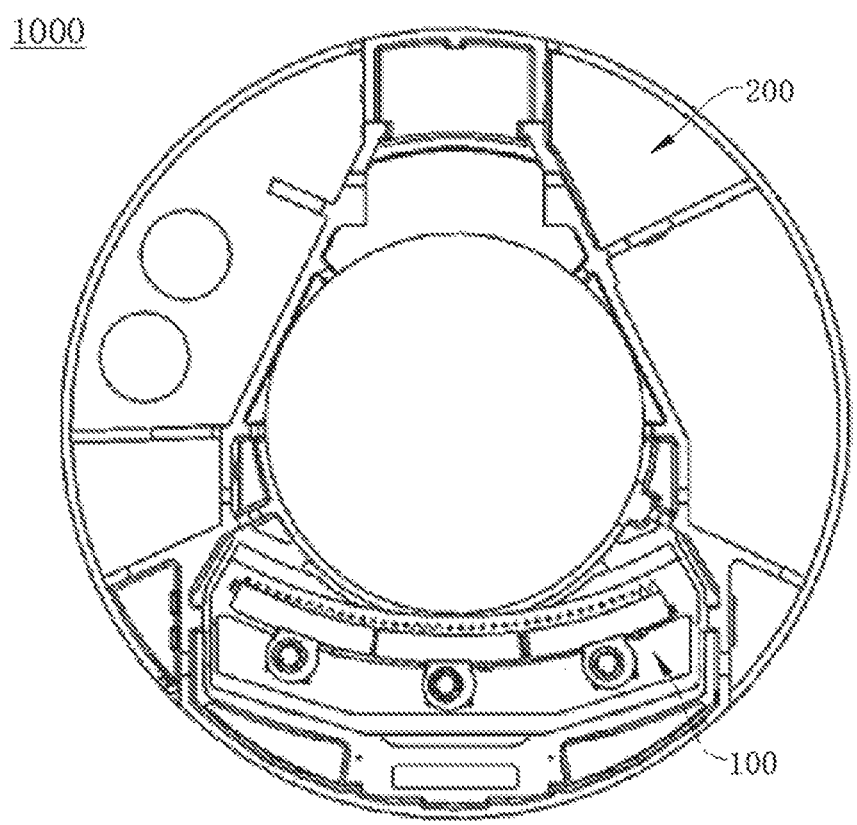
FIG. 15 is a schematic diagram illustrating a structure of an imaging apparatus according to some embodiments of the present disclosure.

FIG. 15 is a schematic diagram illustrating a structure of an imaging apparatus according to some embodiments of the present disclosure. Some embodiments of the present disclosure may provide an imaging apparatus 1000. The imaging apparatus 1000 may include a rotating gantry 200 and a detection apparatus 100. The detection apparatus 100 may be arranged on the rotating gantry 200 as shown in FIG. 15. In some embodiments, the detection apparatus 100, as a whole, may be arranged on the rotating gantry 200. In some embodiments, some components in the detection apparatus 100 (e.g., a third air device, a shunt cover, etc.) may be installed separately. For example, the third air device may be directly arranged on a free space of the rotating gantry 200, and be connected with other components of an air guiding assembly through an air supplying duct, thus the space utilization may be maximized.

The possible beneficial effects of the detection apparatus and the imaging apparatus provided in some embodiments of the present disclosure may include but may not be limited to: (1) the detection apparatus provided in some embodiments of the present disclosure may divide the installation chamber into a plurality of sections in one or more directions, and the temperature may be controlled for different sections, thus the heat dissipation efficiency of the one or more detection units may be effectively improved, the temperature gradient of the detection unit(s) may be reduced, and the stability and detection accuracy of the one or more detection unit(s) may be improved; (2) the detection apparatus provided in some embodiments of the present disclosure may utilize an air duct to directly supply air flow into the installation chamber, thus the air flow may directly contact components that need to dissipate heat, thus the utilization rate of the air flow may be improved and the heat dissipation efficiency may be ensured; (3) the detection apparatus provided in some embodiments of the present disclosure may allow the air flow to take away the heat transferred by the heat conduction of the detection assembly and the heat inside the sections at the same time through a plurality of air duct structures, thus the stability of the working environment temperature may be maintained and the image quality may be ensured. It should be noted that different embodiments may produce different beneficial effects. In different embodiments, the possible beneficial effects may be any one or a combination of the above, or any other possible beneficial effects.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Meanwhile, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, the numbers expressing quantities of ingredients, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Finally, it should be understood that the embodiments described in the present disclosure merely illustrates the principles of the embodiments of the present disclosure. Other modifications may be within the scope of the present disclosure. Accordingly, by way of example, and not limitation, alternative configurations of embodiments of the present disclosure may be considered to be consistent with the teachings of the present disclosure. Accordingly, the embodiments of the present disclosure are not limited to the embodiments explicitly introduced and described by the present disclosure.

What is claimed is:

1. A detection apparatus, comprising:
a housing assembly configured to connect the detection apparatus to a gantry;
an installation chamber including an air inlet and an air outlet, wherein the installation chamber is formed in the housing assembly, the air inlet is arranged on a first side wall of the housing assembly, and the air outlet is arranged on a second side wall opposite to the first side wall of the housing assembly, and the installation chamber is divided by one or more diaphragms into at least two sections;
one or more detection units arranged in the installation chamber; and
a cooling assembly configured to cool the one or more detection units.

2. The detection apparatus of claim 1, wherein the installation chamber is divided by the one or more diaphragms which are arranged along a direction of the one or more detection units.

3. The detection apparatus of claim 2, wherein the installation chamber is divided into three sections along a length direction of the one or more detection units, and the three sections include a middle section, and two side sections located on both sides of the middle section, each of the middle section and the two side sections contains at least a portion of the one or more detection units.

4. The detection apparatus of claim 3, wherein a count of air inlets arranged on a unit area of the middle section exceeds a count of air inlets arranged on a unit area of the two side sections, and cooling performance parameters of the cooling assembly acting on the middle section are greater than the cooling performance parameters of the cooling assembly acting on the two side sections.

5. The detection apparatus of claim 1, wherein the installation chamber is divided by the one or more diaphragms into the at least two sections along a height direction of the one or more detection units.

6. The detection apparatus of claim 5, wherein the detection apparatus further comprises:
a first diaphragm configured to divide the installation chamber into a first heat dissipation section and a second heat dissipation section;
a first air assembly configured to dissipate heat from the first heat dissipation section; and
a second air assembly configured to dissipate heat of the second heat dissipation section; wherein
at least a portion of the one or more detection units is contained and fixed in the first heat dissipation section, the at least a portion of the one or more detection units includes a detection assembly, and the rest portions of the one or more detection units are contained and fixed in the second heat dissipation section.

7. The detection apparatus of claim 6, wherein the installation chamber is divided by a baffle assembly into an inlet section and an outlet section, the inlet section and outlet section are respectively connected to opposing sides of the first heat dissipation section, and the first air assembly includes at least one of an inlet air device arranged at the inlet section or an outlet air device arranged at the outlet section.

8. The detection apparatus of claim 6, wherein the rest portions of the one or more detection units include at least a portion of a heat dissipation assembly, the heat dissipation assembly is in thermal contact with the detection assembly, and the at least a portion of the heat dissipation assembly extends to the second heat dissipation section; or
an extension direction of the first heat dissipation section is perpendicular to an extension direction of the second heat dissipation section.

9. The detection apparatus of claim 8, wherein the heat dissipation assembly includes a support and a heat dissipation structure arranged on the support, the support is in thermal contact with the detection assembly, and air flow generated by the second air assembly flows in a direction parallel to a main heat dissipation plane of the support.

10. The detection apparatus of claim 8, wherein,
the at least a portion of the one or more detection units includes a first circuit board module, the first circuit board module being electrically connected and in thermal contact with the detection assembly; and
the rest portions of the one or more detection units include a second circuit board module, the second circuit board module being electrically connected with the first circuit board module and in thermal contact with the support.

11. The detection apparatus of claim 1, wherein the cooling assembly includes an air guiding assembly, the air guiding assembly includes one or more air ducts, and at least one outlet end of the one or more air ducts is connected with the air inlet of the installation chamber.

12. The detection apparatus of claim 11, wherein the air guiding assembly includes a third air device, and air flow generated by the third air device enters the installation chamber via the one or more air ducts.

13. The detection apparatus of claim 12, wherein the air guiding assembly includes a shunt cover arranged between the third air device and the one or more air ducts, the shunt cover is provided with one or more air outlet holes, and the one or more air outlets are arranged on a side wall of the shunt cover perpendicular to a flow direction of the air flow generated by the third air device, and at least one inlet end of the one or more air ducts is connected with at least one of the one or more air outlet holes.

14. The detection apparatus of claim 11, wherein a count of the air inlet is one or more, which are arranged on at least one of a side wall or a top wall of the installation chamber, and the one or more air inlets are arranged corresponding to a gap between two adjacent detection units of the one or more detection units.

15. The detection apparatus of claim 2, wherein
a first air duct is formed between at least one of the one or more detection units and a top wall of the installation chamber, and a second air duct and a third air duct through the at least one of the one or more detection units are arranged on one side of the at least one of the one or more detection units;
the first air duct and the second air duct are both connected with the air inlet, and the third air duct is connected with the first air duct; and
the second air duct and the third air duct are both connected with the air outlet.

16. The detection apparatus of claim 1, wherein the cooling assembly includes an air guiding assembly, and the air guiding assembly includes a plurality of air ducts;
the installation chamber is provided with one or more diaphragms configured to divide the installation chamber into at least two sections, there being a plurality of air inlets; and
at least one of the at least two sections is connected with a portion of the plurality of air ducts through a corresponding air inlet on the installation chamber.

17. The detection apparatus of claim 16, wherein
when the at least two sections are arranged along a direction of the one or more detection units, the cooling performance parameters of the cooling assembly acting on a middle section are greater than the cooling performance parameters of the cooling assembly acting on at least one of the two side sections; and
when the at least two sections are arranged along a height direction of the one or more detection units, the cooling performance parameters of the cooling assembly acting on a section at an upper position are greater than the cooling performance parameters of the cooling assembly acting on a section at a lower position; wherein
the cooling performance parameters of the cooling assembly includes at least one of a count of the air ducts, a count of air devices, and a speed of air devices corresponding to a section.

18. The detection apparatus of claim 1, wherein
the detection apparatus further comprises temperature sensors arranged in different sections configured to detect temperatures of different sections, and the cooling performance parameters of the cooling assembly acting on each section are adjusted based on a temperature of a corresponding section.

19. An imaging apparatus, comprising:
a gantry; and
a detection apparatus, wherein the detection apparatus is arranged on the gantry, the detection apparatus including:
a housing assembly configured to connect the detection apparatus to the gantry;
an installation chamber including an air inlet and an air outlet, wherein the installation chamber is formed in the housing assembly, the air inlet is arranged on a first side wall of the housing assembly, and the air outlet is arranged on a second side wall opposite to the first side wall of the housing assembly, and the installation chamber is divided by one or more diaphragms into at least two sections;
one or more detection units arranged in the installation chamber; and
a cooling assembly configured to cool the one or more detection units.

* * * * *